United States Patent
Cote et al.

(10) Patent No.: US 8,814,893 B2
(45) Date of Patent: Aug. 26, 2014

(54) SURGICAL KNIFE SAFETY HANDLE HAVING USER OPERABLE LOCK

(75) Inventors: Dana M. Cote, Saugus, MA (US); Brian D. Rapp, Nashua, NH (US); Paul E. Karnafel, Foxborough, MA (US); Xiaoyu Zhang, Chestnut Hill, MA (US)

(73) Assignee: Beaver-Visitec International (US), Inc., Lake Forest, IL (US)

( * ) Notice: Subject to any disclaimer, the term of this patent is extended or adjusted under 35 U.S.C. 154(b) by 0 days.

(21) Appl. No.: 12/929,008

(22) Filed: Dec. 22, 2010

(65) Prior Publication Data
US 2011/0092995 A1    Apr. 21, 2011

Related U.S. Application Data

(63) Continuation of application No. 11/252,575, filed on Oct. 19, 2005, now Pat. No. 7,909,840.

(60) Provisional application No. 60/619,958, filed on Oct. 20, 2004.

(51) Int. Cl.
| | |
|---|---|
| *A61B 17/32* | (2006.01) |
| *A61B 17/3211* | (2006.01) |
| *A61F 9/013* | (2006.01) |
| *A61F 9/007* | (2006.01) |
| *A61B 19/00* | (2006.01) |

(52) U.S. Cl.
CPC ............ *A61B 17/3211* (2013.01); *A61F 9/0133* (2013.01); *A61F 9/00754* (2013.01); *A61B 2019/4805* (2013.01); *A61B 2017/32113* (2013.01)
USPC .............................................. 606/167; 30/286

(58) Field of Classification Search
CPC ................. A61B 17/3211; A61B 2017/32113; A61B 2019/4805; A61F 9/0133; A61F 9/00754
USPC ............ 606/166–167, 172; 30/286, 289–295, 30/330–339
See application file for complete search history.

(56) References Cited

U.S. PATENT DOCUMENTS

| | | |
|---|---|---|
| 1,195,169 A | 8/1916 | Adcock |
| 1,914,153 A | 6/1933 | Ogden |

(Continued)

FOREIGN PATENT DOCUMENTS

| | | |
|---|---|---|
| DE | 3722899 | 1/1989 |
| EP | 0 162 170 | 11/1985 |

(Continued)

OTHER PUBLICATIONS

Oasis Medical Inc., "Oasis Priemier Shield Safety Scalpels," Oasis Product Catalog, 2006, Glendora California.

(Continued)

*Primary Examiner* — Gregory Anderson
(74) *Attorney, Agent, or Firm* — Roylance, Abrams, Berdo and Goodman, LLP

(57) ABSTRACT

A surgical knife safety device having a handle, a blade connected to the handle, and a guard carried by the handle for sliding movement between a retracted position in which the blade is exposed for use, and an extended position for covering the sharp cutting edge of the blade. In the retracted position, an enlarged guard radius is provided at the distal end of the handle to allow improved handle control and blade orientation. The enlarged guard radius is positioned to allow the user to firmly grip a large distal handle portion which is preferably molded as a single piece with the blade holder, preventing unwanted blade or handle movement due to guard mechanism tolerances. A spring, such as leaf spring or a cantilever beam, and a pair of detents or slots are provided to fix the guard in the extended or retracted position and to provide resistance during movement between the two positions.

30 Claims, 20 Drawing Sheets

(56) References Cited

U.S. PATENT DOCUMENTS

| | | |
|---|---|---|
| 2,207,296 A | 7/1940 | Lee |
| 2,304,332 A | 12/1942 | Bodkin |
| 2,512,237 A | 6/1950 | Mravik |
| 2,885,779 A | 5/1959 | Newkirk |
| 2,885,780 A | 5/1959 | Campbell |
| 2,896,317 A | 7/1959 | Vaive |
| 3,176,395 A | 4/1965 | Warner et al. |
| 3,192,624 A | 7/1965 | Gringer |
| 3,383,763 A | 5/1968 | Strandfors |
| 3,518,758 A | 7/1970 | Bennett |
| 3,706,106 A | 12/1972 | Leopoldi |
| 3,905,101 A | 9/1975 | Shepherd |
| 3,906,626 A | 9/1975 | Riuli |
| 3,943,627 A | 3/1976 | Stanley, Jr. |
| 3,967,377 A | 7/1976 | Wells |
| 4,091,537 A | 5/1978 | Stevenson, Jr. |
| 4,096,629 A | 6/1978 | Levine |
| 4,265,017 A | 5/1981 | Collins |
| 4,356,631 A | 11/1982 | Guth |
| 4,375,218 A | 3/1983 | DiGeronimo |
| 4,393,587 A | 7/1983 | Kloosterman |
| 4,414,974 A | 11/1983 | Dotson et al. |
| 4,491,132 A | 1/1985 | Aikins |
| 4,499,898 A | 2/1985 | Knepshield et al. |
| 4,500,220 A | 2/1985 | Hashimoto |
| 4,516,575 A | 5/1985 | Gerhard et al. |
| 4,523,379 A | 6/1985 | Osterhout et al. |
| 4,538,356 A | 9/1985 | Knepshield et al. |
| 4,576,164 A | 3/1986 | Richeson |
| D283,544 S | 4/1986 | Schmidt et al. |
| 4,630,378 A | 12/1986 | Kulp et al. |
| 4,660,287 A | 4/1987 | Decker |
| 4,662,075 A | 5/1987 | Mastel et al. |
| 4,719,915 A | 1/1988 | Porat et al. |
| 4,735,202 A | 4/1988 | Williams |
| 4,757,612 A | 7/1988 | Peyrot |
| 4,815,218 A | 3/1989 | Gordy |
| 4,823,457 A | 4/1989 | Prochaska |
| 4,825,545 A | 5/1989 | Chase et al. |
| 4,826,339 A | 5/1989 | Sasaki |
| 4,910,821 A | 3/1990 | Kieferle |
| 4,958,625 A | 9/1990 | Bates et al. |
| 4,985,034 A | 1/1991 | Lipton |
| 5,015,252 A | 5/1991 | Jones |
| 5,035,703 A | 7/1991 | Baskas |
| 5,071,426 A | 12/1991 | Dolgin et al. |
| 5,139,507 A | 8/1992 | Dolgin et al. |
| 5,201,748 A | 4/1993 | Newman et al. |
| 5,203,865 A | 4/1993 | Siepser |
| 5,207,696 A | 5/1993 | Matwijcow |
| 5,222,951 A | 6/1993 | Abidin et al. |
| 5,250,063 A | 10/1993 | Abidin et al. |
| 5,254,128 A | 10/1993 | Mesa |
| 5,275,606 A | 1/1994 | Abidin et al. |
| 5,292,329 A | 3/1994 | Werner |
| 5,299,357 A | 4/1994 | Wonderley et al. |
| 5,309,641 A | 5/1994 | Wonderley et al. |
| 5,312,429 A | 5/1994 | Noack |
| 5,330,492 A | 7/1994 | Haugen |
| 5,330,493 A | 7/1994 | Haining |
| 5,330,494 A | 7/1994 | Vander Westhuizen et al. |
| 5,336,235 A | 8/1994 | Myers |
| 5,342,379 A | 8/1994 | Volinsky |
| 5,344,424 A | 9/1994 | Roberts et al. |
| 5,352,220 A | 10/1994 | Abidin et al. |
| 5,361,902 A | 11/1994 | Abidin et al. |
| 5,370,654 A | 12/1994 | Abidin et al. |
| 5,411,512 A * | 5/1995 | Abidin et al. ............. 606/167 |
| 5,417,704 A | 5/1995 | Wonderley |
| 5,431,672 A | 7/1995 | Cote et al. |
| 5,433,321 A | 7/1995 | Abidin et al. |
| 5,475,925 A | 12/1995 | Newman et al. |
| 5,496,340 A | 3/1996 | Abidin et al. |
| 5,507,762 A | 4/1996 | Abidin et al. |
| 5,528,811 A | 6/1996 | Abidin et al. |
| 5,531,754 A | 7/1996 | Shackelford, Sr. et al. |
| 5,545,175 A | 8/1996 | Abidin et al. |
| 5,569,281 A | 10/1996 | Abidin et al. |
| 5,571,127 A | 11/1996 | DeCampli |
| 5,577,850 A | 11/1996 | Mishima |
| 5,601,572 A | 2/1997 | Middleman et al. |
| 5,613,300 A | 3/1997 | Schmidt |
| 5,620,454 A | 4/1997 | Pierce et al. |
| 5,662,221 A | 9/1997 | Abidin et al. |
| 5,662,669 A | 9/1997 | Abidin et al. |
| 5,664,668 A | 9/1997 | Zainal et al. |
| 5,665,099 A | 9/1997 | Pilo et al. |
| D386,526 S | 11/1997 | Ito |
| 5,683,407 A | 11/1997 | Jolly et al. |
| 5,727,682 A | 3/1998 | Abidin et al. |
| 5,741,289 A | 4/1998 | Jolly et al. |
| 5,749,886 A | 5/1998 | Abidin et al. |
| 5,752,968 A | 5/1998 | Jolly et al. |
| 5,792,162 A | 8/1998 | Jolly et al. |
| 5,827,309 A | 10/1998 | Jolly et al. |
| 5,830,226 A | 11/1998 | Webb et al. |
| 5,908,432 A | 6/1999 | Pan |
| 5,919,201 A | 7/1999 | Carter et al. |
| 5,924,206 A | 7/1999 | Cote et al. |
| 5,938,676 A | 8/1999 | Cohn et al. |
| D421,303 S | 2/2000 | Cote et al. |
| 6,053,929 A | 4/2000 | Cohn et al. |
| 6,065,889 A | 5/2000 | Maruyama et al. |
| 6,079,106 A | 6/2000 | Vallotton |
| 6,089,775 A | 7/2000 | Yokouchi |
| 6,112,420 A | 9/2000 | Schickerling |
| 6,254,621 B1 | 7/2001 | Shackelford et al. |
| 6,391,041 B1 | 5/2002 | Edens |
| D463,555 S | 9/2002 | Etter et al. |
| D465,279 S | 11/2002 | Etter et al. |
| D466,214 S | 11/2002 | Otsuka |
| 6,503,262 B1 | 1/2003 | Edens |
| D470,938 S | 2/2003 | Howell et al. |
| 6,569,175 B1 | 5/2003 | Robinson |
| 6,626,925 B2 | 9/2003 | Newman et al. |
| 6,629,985 B1 | 10/2003 | Kiehne |
| D496,730 S | 9/2004 | Morawski et al. |
| 6,854,187 B2 | 2/2005 | Huan |
| D504,513 S | 4/2005 | Morawski et al. |
| 6,884,240 B1 | 4/2005 | Dykes |
| 6,948,250 B1 | 9/2005 | Caiafa, Jr. et al. |
| 7,022,128 B2 | 4/2006 | Morawski et al. |
| 7,055,248 B2 | 6/2006 | Cote |
| 7,121,005 B2 | 10/2006 | Hughes |
| D533,944 S | 12/2006 | Sullivan et al. |
| 7,150,754 B2 | 12/2006 | Ziemer |
| D537,528 S | 2/2007 | Christensen et al. |
| 7,185,435 B1 | 3/2007 | Tseng |
| D571,010 S | 6/2008 | Cote |
| 7,387,637 B2 | 6/2008 | Morawski et al. |
| 7,520,059 B2 | 4/2009 | Ranieri et al. |
| D642,682 S | 8/2011 | Chaudhary et al. |
| 8,256,330 B2 | 9/2012 | Auchter et al. |
| 8,256,331 B2 | 9/2012 | Auchter et al. |
| 2002/0065532 A1 | 5/2002 | Harrold et al. |
| 2002/0143352 A1 | 10/2002 | Newman et al. |
| 2003/0225428 A1 | 12/2003 | Saito et al. |
| 2004/0215174 A1 | 10/2004 | Morawski et al. |
| 2005/0015104 A1 | 1/2005 | Morawski et al. |
| 2005/0119680 A1 | 6/2005 | Dykes |
| 2005/0138816 A1 | 6/2005 | Ping |
| 2005/0267502 A1 | 12/2005 | Hochman |
| 2006/0085019 A1 | 4/2006 | Cote et al. |
| 2009/0204136 A1 | 8/2009 | Endo |

FOREIGN PATENT DOCUMENTS

| | | |
|---|---|---|
| EP | 0 555 196 | 8/1993 |
| EP | 0 653 190 | 5/1995 |
| EP | 0 701 798 | 3/1996 |
| TW | 244896 | 4/1995 |

(56) References Cited

FOREIGN PATENT DOCUMENTS

| WO | WO 85/01431 | 4/1985 |
| WO | WO 93/01755 | 2/1993 |
| WO | WO 93/11916 | 6/1993 |
| WO | WO 93/21837 | 11/1993 |
| WO | WO 97/37599 | 10/1997 |
| WO | WO 01/05312 A1 | 1/2001 |
| WO | WO 03/099145 | 12/2003 |
| WO | WO 2008/029566 | 3/2008 |

OTHER PUBLICATIONS

Surgistar Website, "881861 Slit 1.8mm Safety Knife Angled", Downloaded Apr. 28, 2011, product p. 1, product enlargement p. 2, www.surgistar.com/product_detail.php?i=839.

Surgistar Advertisement, "Self-Defense / Safety Doesn't Happen By Accident / Introducing The Safety Knife Series From Surgistar", Eurotimes, Feb. 2011, cover page and p. 6, vol. 16, Issue 2.

Surgistar Brochure, "Self-Defense / Safety Doesn't Happen By Accident / Introducing The Safety Knife Series From Surgistar", Copyright 2010, pp. 1 and 2.

\* cited by examiner

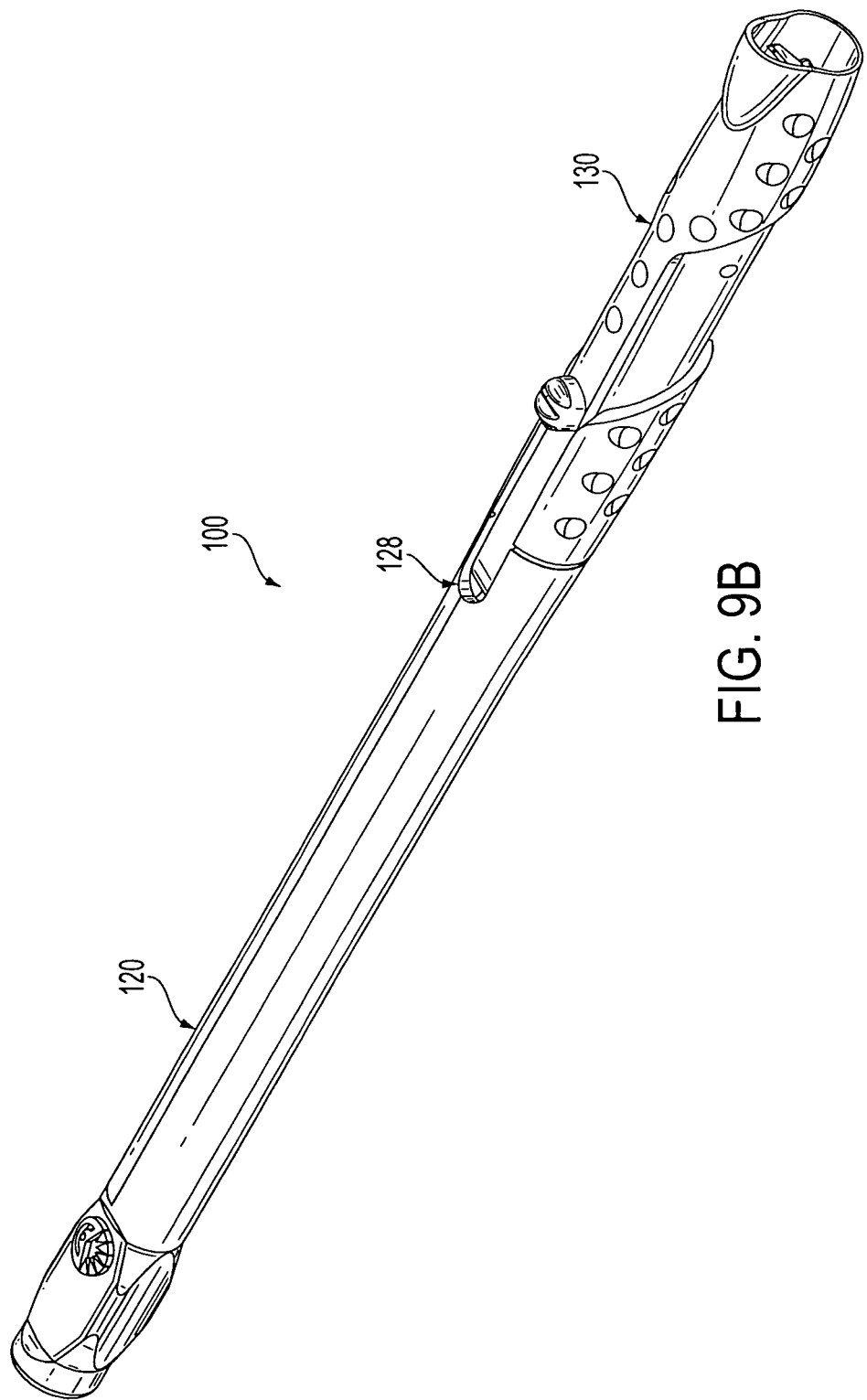

SURGICAL KNIFE SAFETY HANDLE HAVING USER OPERABLE LOCK

CROSS-REFERENCE TO RELATED APPLICATIONS

This is a continuation of U.S. patent application Ser. No. 11/252,575, filed Oct. 19, 2005 now U.S. Pat. No. 7,909,840, entitled "Surgical Knife Safety Handle Having User Operable Lock", which claims the benefit under 35 U.S.C. §119(a) of U.S. Provisional Patent Application Ser. No. 60/619,958, filed Oct. 20, 2004, entitled "Surgical Knife Safety Handle", the entire contents of both applications being incorporated herein by reference.

FIELD OF THE INVENTION

The present invention relates to a system and method for a surgical knife safety handle, for both ophthalmic and non-ophthalmic applications, having a movable guard that can be retracted to expose the blade when in use, and that can be extended to cover the blade when not in use, and including a pushback prevention mechanism and a user operable lock to ensure that the blade is covered until manually exposed.

BACKGROUND OF THE INVENTION

In various surgical procedures, the surgeon typically has to make an incision in the patient in order to remove unwanted tissue, repair damaged tissue, or implant a device to improve the patient's well being. In certain cases, all three of these activities, or a combination thereof, must be done in a single procedure. For example, in cataract surgery, the surgeon removes the natural lens that has been clouded by a cataract from the patient's eye and replaces it with an artificial lens that will improve the patient's eyesight. In order to perform this procedure, an incision is made in the cornea of the eye by the surgeon using a scalpel. This provides the surgeon with access to the patient's lens. The clouded lens is cut loose and removed. There are a number of different procedures that are used to remove a patient's lens that has a cataract. Two of the more common techniques are known as extracapsular surgery and phacoemulsification.

In extracapsular surgery, the surgeon removes the lens leaving behind the back half of the capsule. In phacoemulsification, the surgeon fragments the lens by ultrasonic vibrations and the lens is simultaneously irrigated and aspirated. After the lens is removed, the surgeon then inserts an artificial lens known as an intra-ocular lens (IOL) into the eye either behind or in front of the iris. Two small C-shaped arms connected to the IOL eventually become scarred into the side of the eye and hold the IOL firmly in place.

In another type of ophthalmic procedure known as the Implantable Contact Lens procedure (ICL), the surgeon makes an incision in the patient's eye and implants a contact lens in the eye in front of the existing lens but behind the iris. This corrects the patient's vision so that he or she can see clearly without the need for external contact lenses or eyeglasses.

Typically a nurse or other surgical assistant manages the devices that are used during such delicate surgeries. For example, the assistant ensures that the appropriate sterile devices are available in the operating suite for the particular procedure that is to be performed. With respect to scalpels, the assistant often hands the scalpel to the surgeon in a predetermined orientation so that the surgeon can grip the scalpel's handle without taking his or her eyes away from the patient. This also minimizes the possibility that the surgeon will be cut with the blade on the scalpel. After the surgeon completes the incision, the scalpel is handed back to the assistant for proper disposal or sterilization. While the procedure is being performed, this requires the assistant to place the used scalpel on a particular tray that will be removed after the procedure is completed. The devices on the tray are then disposed of or are sterilized for reuse.

If all appropriate protocols are followed, no hospital personnel will be cut by used or unused scalpel blades. Unfortunately, accidental cuts of hospital personnel do occur for a variety of reasons. For example, because the surgeon and assistant are concentrating on the patient and the procedure being performed on the patient, they may not pay close attention to the scalpels. Also, the scalpels may become exposed during shipment or when scalpel packages are dropped or mishandled prior to use. Once opened, the assistant may put the used scalpels in an inappropriate location or, even if the used scalpels are placed on the proper tray, the blade may be exposed to the operating suite personnel. In these situations, the operating suite personnel may inadvertently come into contact with the blade as they move around the patient during the procedure and be cut or nicked by the exposed blade.

Other hospital personnel may also come into contact with such blades and may also be cut or nicked. Usually used blades are disposed of in an appropriate sharps container that allows used needles and blades to be inserted into the container but prevents access by hospital personnel to the sharp end of a needle or the sharp cutting surface of the blade. However, during cleanup of the operating suite, the used blades may be exposed prior to their placement in the appropriate sharps container. If hospital personnel are not paying close attention to their activities or, if the exposed blades are hidden from view because they are buried in a pile of other devices or hospital linen, these hospital personnel may come into contact with the sharp cutting surface of the blade and be cut or nicked.

Cuts and nicks from blades are uncomfortable and distracting at best. In addition, such cuts and nicks from used blades may result in blood or body fluid exposure which can result in the spread of infectious diseases between the patient and hospital personnel. Concern over this situation has become especially acute in recent years because of such diseases as acquired immuno-deficiency syndrome, i.e. AIDS, and hepatitis. These diseases may be transmitted from an infected person to another person by the transmission of body fluids, typically blood.

In view of the need for a scalpel that can at least minimize the chances of accidental cuts or nicks, while also protecting the cutting edge of the blade, numerous scalpels have been designed. These designs typically take the form of a scalpel having a guard that shields the sharp cutting surface of the blade from undesired contact with hospital personnel and surrounding surfaces. The guard in these devices can be extended to a position shielding the blade or retracted exposing the blade for use. Alternatively, the scalpel may be designed to allow the blade to move into or out of the scalpel handle, to either shield or expose the sharp cutting surface.

Unfortunately, these designs are deficient because they tend to be cumbersome and difficult to use, and because they may cause unwanted shielding or exposure of the blade prior to the need for such shielding or exposure. Also, such devices may require considerable attention by the user to shield or expose the blade. Additionally, the shield may distort the handle outline when retracted, making the handle difficult to hold or control. Any design which allows the blade to move, for retraction or extension design purposes, also introduces concerns regarding exact blade positioning and rigidity during use. Such concerns also apply in cases in which the user is required to hold the retracted shield as a grip, allowing any movement between shield and handle to possibly result in unwanted movement of the blade.

Accordingly, a need exists for a device and method to provide a shielding mechanism that is simple to use and remains in a shielding position until disengaged by the user, even during shipping and when mishandled or dropped prior to opening. The handle and shielding mechanism should also provide a uniform gripping surface when retracted, allowing user control of the scalpel without any unwanted gripping surface or blade movement.

SUMMARY OF THE INVENTION

It is therefore an object of embodiments of the present invention to provide a device and method that may be used to shield and protect a sharp blade, such as a scalpel, and minimize the chances of cuts or nicks during shipping, handling or disposal.

It is another object of embodiments of the present invention to provide a device and method that is easy to use and that can be operated by one hand of the user.

It is another object of embodiments of the present invention to provide a device and method that will substantially prevent the shield from becoming accidentally displaced when fully extended and exposing the blade.

It is another object of embodiments of the present invention to provide a device and method that will substantially prevent the shield from becoming accidentally displaced and exposing the blade during shipping.

It is another object of embodiments of the present invention to provide a device and method that will substantially prevent the shield from becoming accidentally displaced and exposing the blade during mishandling when packaged.

It is another object of embodiments of the present invention to provide a device and method comprising a pushback prevention mechanism that will substantially prevent the shield from becoming accidentally displaced and exposing the blade when a force is applied to the fully extended shield.

It is another object of embodiments of the present invention to provide a device and method comprising a user operable lock that will substantially prevent the shield from becoming accidentally displaced and exposing the blade until intentionally released by a user.

It is another object of embodiments of the present invention to provide a device and method comprising a drop-force operable lock that will substantially prevent the shield from becoming accidentally displaced and exposing the blade when a drop force or impact force is applied to the device end opposite to the shield.

It is another object of embodiments of the present invention to provide a device and method that will allow the user to manually release the user operable lock securing the shield and retract the shield to expose the blade with a single hand.

It is another object of embodiments of the present invention to provide a device and method which maintains an uninterrupted handle surface contour during use, which allows the user better control and orientation of the device.

These and other objects are substantially achieved by providing, in accordance with embodiments of the present invention, a device comprising a handle, a blade connected to the handle, and a guard slidably mounted partially within the handle for sliding movement between a retracted position in which the blade is exposed for use, and an extended position for covering the sharp cutting edge of the blade. In the retracted position, an exposed guard radius is provided at the distal end of the handle to allow improved handle control and blade orientation. The exposed guard radius however, is positioned to allow the user to firmly grip a large distal handle portion which is molded as a single piece with the blade holder, preventing unwanted blade or handle movement due to guard mechanism tolerances.

In accordance with embodiments of the present invention, a leaf spring or cantilever beam, and detents are provided to fix the guard in the extended and retracted position, and to provide slight resistance during movement between each position. Additionally, a pushback prevention mechanism and a user operable lock are incorporated with the guard to prevent accidental retraction from the fully extended position. The pushback prevention mechanism comprises a conical surface slidably positioned within a collet-like guard opening to expand under certain conditions and prevent guard displacement when fully extended except through drive mechanism control. The user operable lock comprises a cantilever beam and projection for engagement with a handle body detent to substantially secure the guard in a fully extended position until intentionally released by the user. The drop-force operable lock can be provided as a rod and button extending from the proximal end of the device to transfer any drop force or impact force to the guard to prevent guard movement. The above and other objects and advantages of the present invention will be apparent upon consideration of the following detailed description.

BRIEF DESCRIPTION OF THE DRAWINGS

The above and other objects and advantages will become apparent upon consideration of the following drawings and detailed description. The preferred embodiments of the present invention are illustrated in the appended drawings in which like reference numerals refer to like elements and in which:

FIG. 9B is a perspective view of the embodiment of FIG. 9A with the guard in an extended position to shield the blade;

In the drawing figures, it will be understood that like numerals refer to like structures.

DETAILED DESCRIPTION OF THE EXEMPLARY EMBODIMENTS

The embodiments of the present invention described below comprise a surgical knife safety handle, for both ophthalmic and non-ophthalmic applications, having a movable guard that can be retracted to expose the blade when in use, and that can be extended to cover the sharp cutting edge of the blade when not in use. The guard is located at a distal end of the handle, partially extending from inside the handle, and including a larger diameter shielding end which becomes part of the exposed handle when fully retracted. When fully extended, the guard covers the exposed cutting edge of the blade without distorting handle contours. The guard is engaged with a drive mechanism slidably mounted within the handle body, which includes a leaf spring or flexible cantilever beam for engaging detents at fully extended and fully retracted positions, and providing audible and tactile engagement feedback. The engagement between the guard and drive mechanism also includes a pushback prevention mechanism comprising a conical surface slidably positioned within a collet-like guard opening to substantially prevent guard displacement when fully extended except through drive mechanism control. Additionally, embodiments of the present invention can further include a user operable lock between the guard drive mechanism and the handle body to substantially prevent undesired guard drive mechanism movement, such as undesired movement occurring during shipment or package mishandling. Still further, embodiments of the present invention can include a drop-force operable lock to substantially prevent undesired guard drive mechanism movement when a sudden force or impact is applied to a device end opposite the guard.

Figure 1:
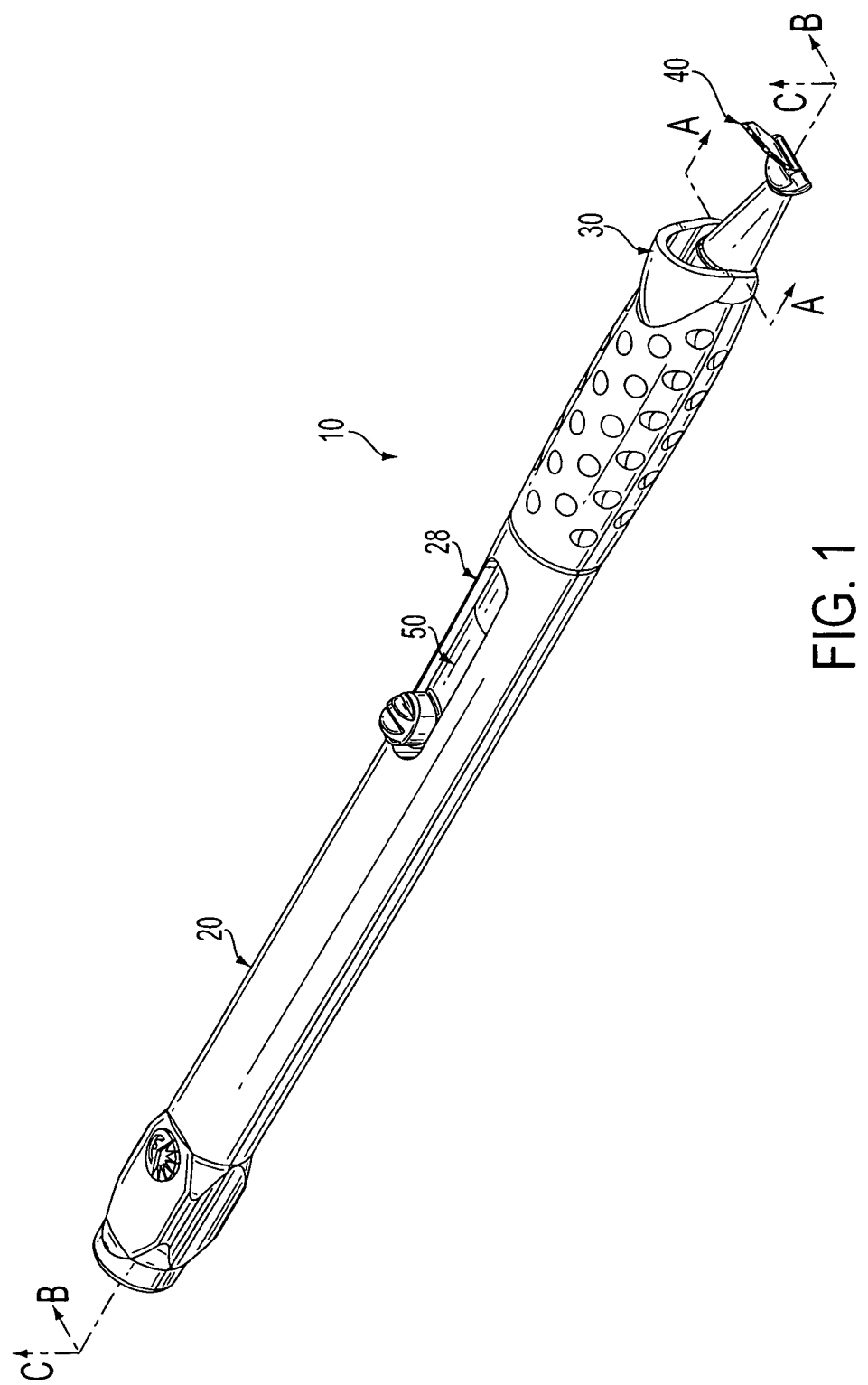
FIG. 1 is a perspective view of an embodiment of the present invention with the guard in a retracted position to expose the blade.

As shown in FIG. 1, the surgical knife safety handle 10 of a first embodiment of the present invention includes a body 20 having a guard 30 slidably received partially within body 20 for longitudinal sliding movement between a retracted and extended position. FIG. 1 is a perspective view of an embodiment of the present invention with the guard 30 in a retracted position to expose a blade 40 for use. The guard 30, when in the retracted position, forms a smooth, uninterrupted handle surface between distal and proximal ends, which is preferred by users of such devices when in use. Additionally, the enlarged guard portion, external to body 20 when fully retracted, defines a noncircular contour about the distal end of the surgical knife safety handle 10 which gives the user better control and allows easier blade orientation during use.

As used herein, the term "proximal" refers to a location on the surgical knife safety handle 10 closest to the person using the device handle and farthest from the patient in connection with which the device handle is used. Conversely, the term "distal" refers to a location on the device handle of this invention farthest from the person using the device handle and closest to the patient in connection with which the device handle is used.

Figure 2:
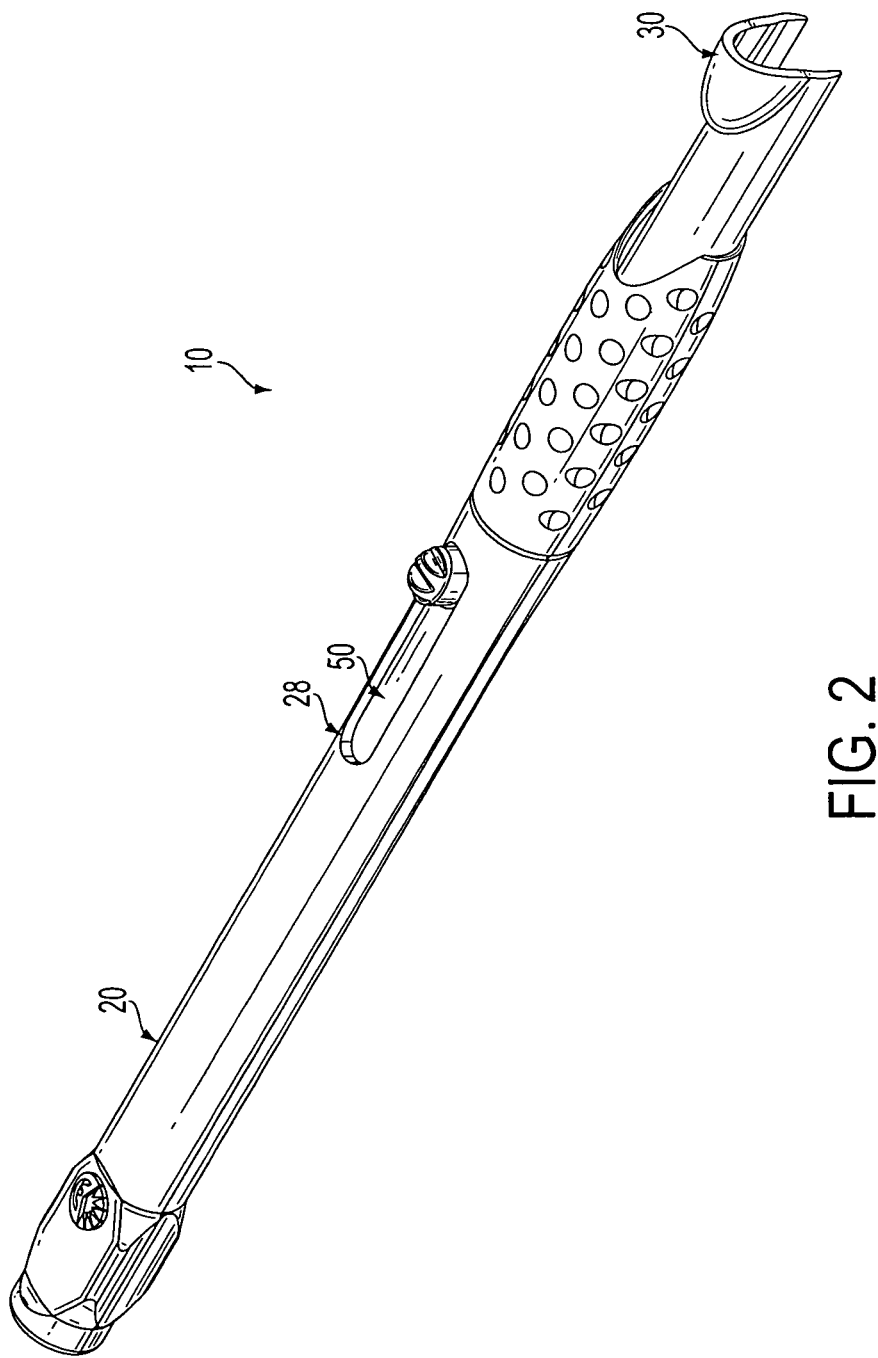
FIG. 2 is a perspective view of the embodiment of FIG. 1 with the guard in an extended position to shield the blade.

The surgical knife safety handle 10 of the present invention also includes a blade 40, or similar device, fixedly secured to the distal end of body 20. However, as stated earlier, exposed blades such as this present several hazards, including accidental cuts of hospital personnel and blade damage. To prevent this, the guard 30 can be slideably extended from the distal end of body 20 to shield the exposed blade 40 as shown in FIG. 2. FIG. 2 is a perspective view of the embodiment of FIG. 1 with the guard 30 in an extended position. A leaf spring and pushback prevention mechanism is employed within the body 20 to prevent unwanted movement of the guard 30 when fully extended, as described in greater detail below.

Figure 3A:
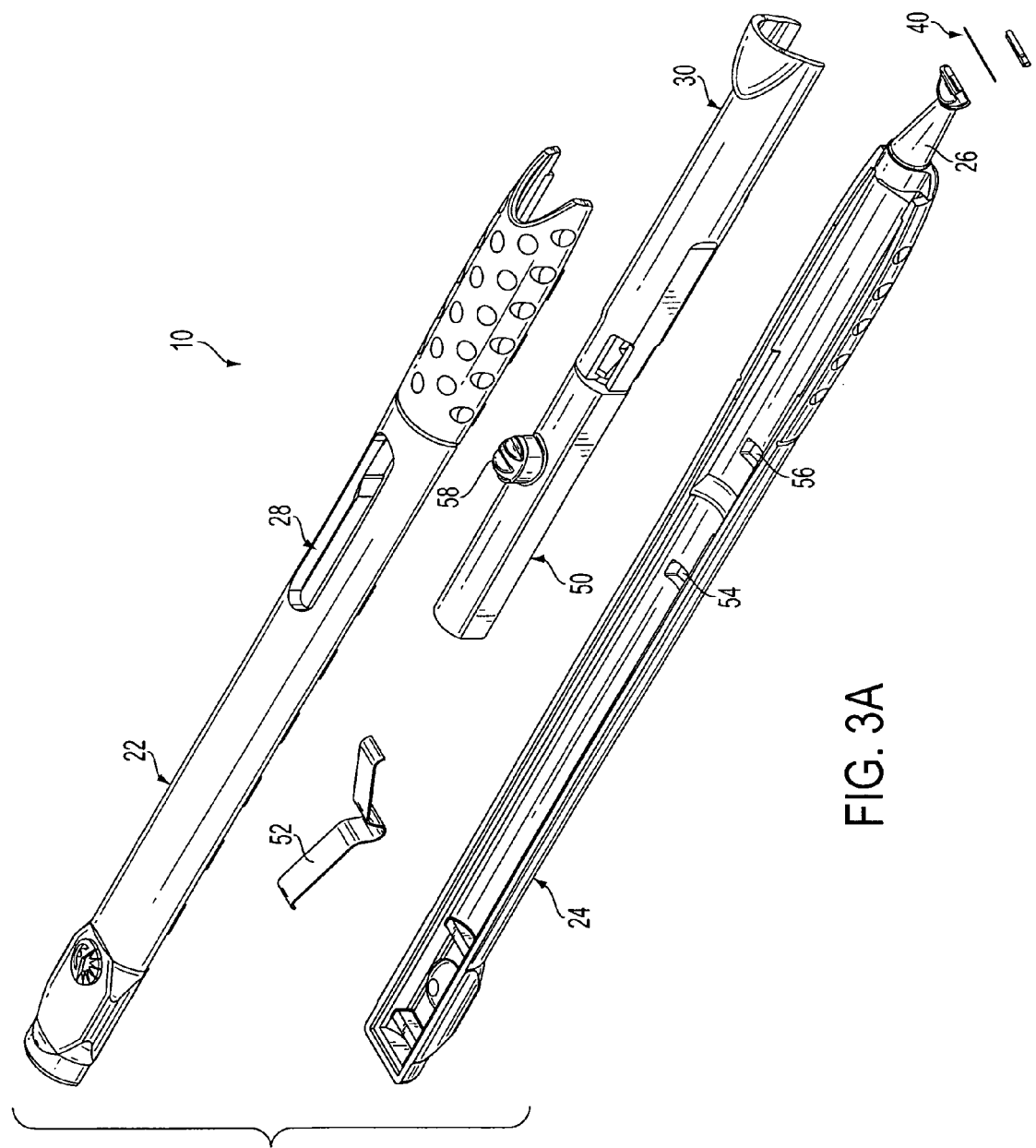
FIG. 3A is an exploded perspective view of the embodiment of FIG. 1.

FIG. 3A is an exploded perspective view of the embodiment of FIG. 1. The view of FIG. 3A includes an upper body contour wall 22 and a lower body contour wall 24, formed to assemble as a handle body 20 and define a substantially hollow chamber within the body 20 to house a guard positioning mechanism 50 and a concealable portion of the guard 30.

The upper body' contour wall 22 includes a slot 28 accessing the chamber to allow protrusion of a raised operator control 58 for the guard positioning mechanism 50, which can be collectively referred to as a user actuator. The upper body contour wall can further include a detent (not shown) for use with a user operable lock to ensure that the blade remains covered until manually exposed. An exemplary embodiment of the user operable lock is described in greater detail below with reference to FIG. 8G.

The distal end of the upper body contour wall 22 also includes an outer surface having a dimpled texture, extending from the distal end of the upper body contour wall 22 to a point slightly before the access slot 28. The textured surface is sufficient to provide the user with a nonslip grip during use, and is duplicated in a similar position on the lower body contour wall 24 such that when assembled, the textured surface appears uniform about an outside diameter of the body 20 near the distal end. Although a dimpled surface is shown in the embodiment in FIG. 3A, any nonslip surface can be used. Additionally, the nonslip surface can be extended or modified from the area shown and described in FIG. 3A as required in other embodiments.

The distal end of the upper body contour wall 22 further includes a semicircular mating port, extending rearward from the distal end, and providing a position in which the raised contoured surface of the exposed portion of the guard 30 is seated when fully retracted. In the fully retracted position, the mating port and exposed guard portion of the guard 30 are configured to provide the smooth, uninterrupted handle surface and noncircular contour about the distal end as described above.

The upper body contour wall 22 and lower body contour wall 24 assemble to form the handle body 20 and define a substantially hollow chamber within the body 20 to house a guard positioning mechanism 50 and a concealable portion of guard 30. The guard positioning mechanism 50, which is described in greater detail below and shown in FIG. 5A, has a generally cylindrical cross section and is sized to slidably fit within the hollow chamber within the body 20. The guard positioning mechanism 50 is controlled to travel between a fully extended and fully retracted position via an external protrusion 58 accessed through channel 28. Each position is maintained by an engagement between a leaf spring 52, which is contained within a body cavity of the guard positioning mechanism 50, and either a first or second detent 54 and 56 in the lower body contour wall 24 as described below. In another embodiment of the present invention described in greater detail below, the guard positioning mechanism 50 further includes a user operable lock to assist in maintaining the guard in a fully extended position. In still another embodiment of the present invention described in greater detail below, the guard positioning mechanism 50 further includes a drop-force operable lock to assist in maintaining a fully extended position.

The lower body contour wall 24 includes a first and second detent 54 and 56 to engage the leaf spring 52 of the guard positioning mechanism 50, locking the guard in position when fully extended or fully retracted. As noted above, the upper body contour wall 22 and lower body contour wall 24 assemble to define a substantially hollow chamber within the body 20 to house the guard positioning mechanism 50 which contains a leaf spring 52, wherein the leaf spring is oriented within the guard positioning mechanism 50 to firmly press against the lower body contour wall 24 when sliding between extended and retracted positions. The lower body contour wall 24 includes first and second detents 54 and 56, located at opposite positions within the substantially hollow chamber such that the leaf spring engages the first detent 54 when the guard positioning mechanism 50 is in a fully retracted position, and engages the second detent 56 when the guard positioning mechanism 50 is in a fully extended position. Slidable movement of the guard positioning mechanism 50 between positions is opposed with a slight resistance created by the leaf spring 52 contact with the lower body contour wall 24 between detents.

Figure 3B:
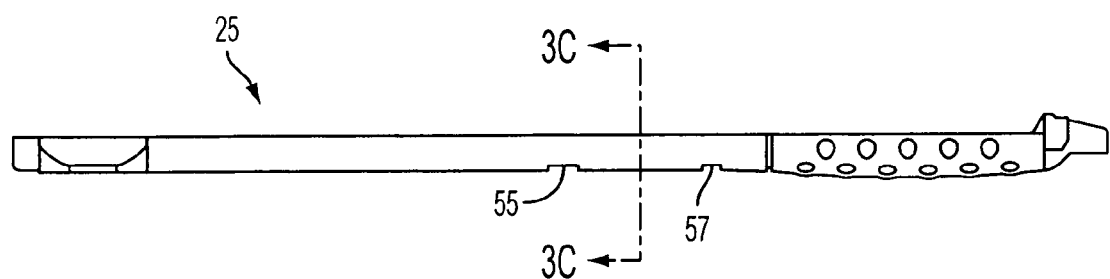
FIG. 3B is a side view of another version of the lower body contour wall having different sized detent openings in accordance with an embodiment of the present invention.
Figure 8A:
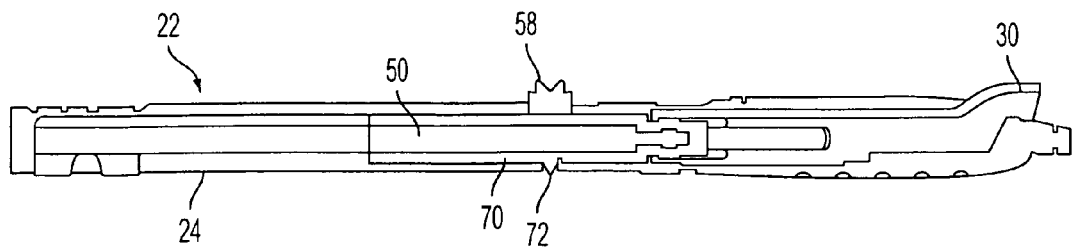
FIG. 8A is a cross-sectional view of a second version of the embodiment of FIG. 1 illustrating a guard positioning mechanism having an integral spring.
Figure 8B:
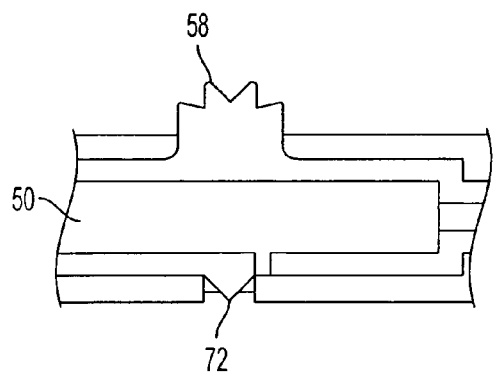
FIG. 8B is an enlarged cross-sectional view of the detent engagement of the integral spring of FIG. 8A.
Figure 8C:
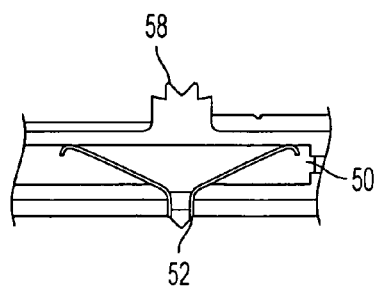
FIG. 8C is an enlarged cross-sectional view of the detent engagement of the leaf spring of FIG. 3A.
Figure 8D:
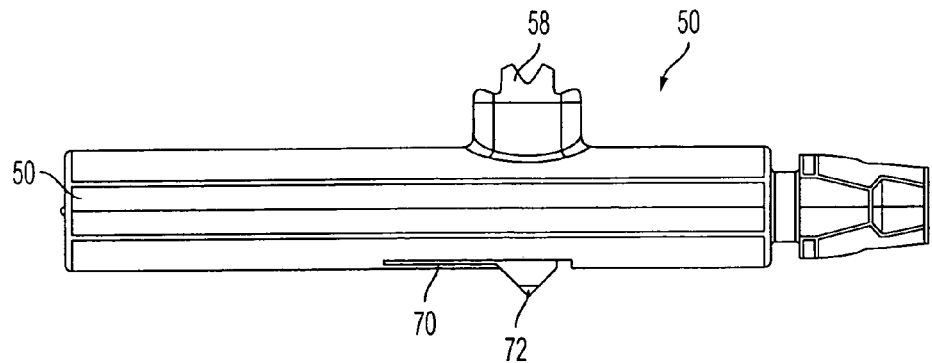
FIG. 8D is an elevational view of the guard positioning mechanism and integral spring of FIG. 8A.
Figure 8E:
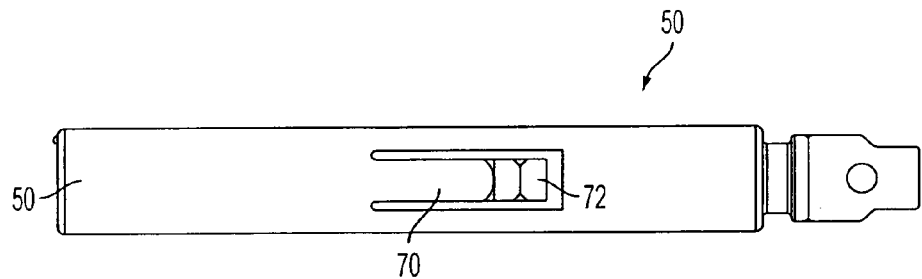
FIG. 8E is a bottom view of the guard positioning mechanism and integral spring of FIG. 8A.
Figure 8F:
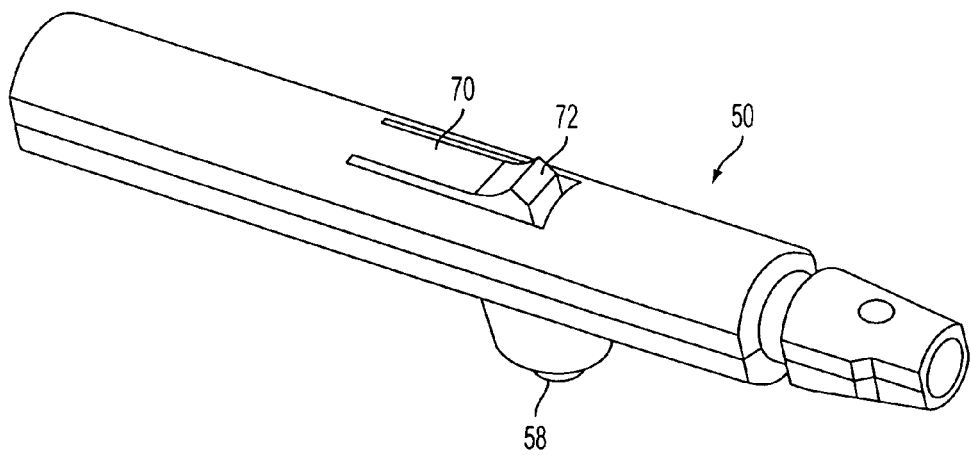
FIG. 8F is a perspective view of the guard positioning mechanism and integral spring of FIG. 8A.
Figure 8G:
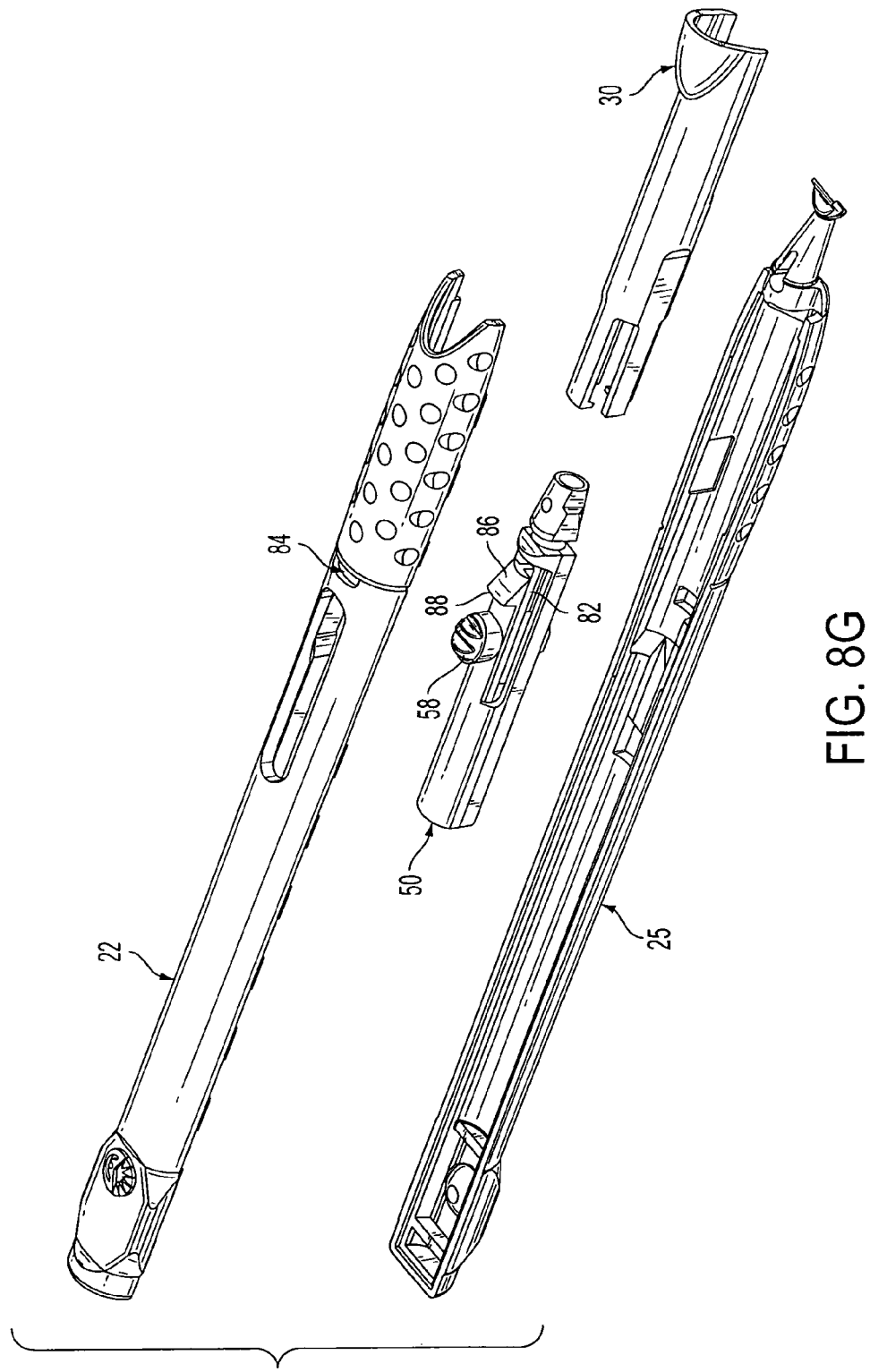
FIG. 8G is an exploded perspective view of another embodiment of the present invention further illustrating a user operable lock.

The detents 54 and 56 can be provided as substantially similar shaped and sized slots in the lower body contour wall 24 as shown in FIG. 3A, or can have varying sizes and dimensions, as shown by the detents 55 and 57 in the lower body contour wall example 25 in FIGS. 3B and 8G. FIG. 3B is a side view of another version of the lower body contour wall having different sized detent openings, and FIG. 8G is an exploded perspective view including the lower body contour wall 25 of FIG. 3B in accordance with another embodiment of the present invention. The smaller detent 57 can be provided to establish a positive engagement force with the leaf spring or an integral cantilever beam as described in greater detail below. As the detent 57 corresponds to the guarded position, the detent opening can be constructed having a smaller opening which engages the spring or beam more securely, that is, holding the spring or beam in a slightly deflected and tensed position, and providing a positive locking force for the guarded position. The detent 55 corresponds to the unguarded, or retracted position and therefore, can be provided having a larger opening. The larger opening of the detent 55 ensures that the spring or beam is more relaxed when engaged and does not take a "set" when in the retracted position. Also, variations in detents 55 and 57 allow for establishing different activation forces required to extend and retract the guard positioning mechanism 50.

The engagement between spring and either detent also provides audible and tactile engagement feedback to the user. The engagement produces an audible sound, such as a "click", when fully extended or fully retracted, and the spring is properly engaged. Also, the proper engagement also produces a mechanical vibration pulse, or tactile feedback, which allows the user to ensure engagement has occurred.

As shown in FIG. 3A, the distal end of the lower body contour wall 24 also includes a tapered blade holder 26, or post, configured to fixedly secure the blade 40 to the distal end of body 20. The tapered blade holder 26 is molded as an extension of the lower body contour wall 24 distal end and has a generally circular cross section area at a point of attachment, and is tapered slightly to a reduced cross section area at a point of attachment to the blade 40, which can be epoxy bonded to the tapered blade holder. Additional details of blade attachment are disclosed in U.S. patent application Ser. No. 10/835,286, the entire disclosure of which is incorporated herein by reference.

Figure 4:
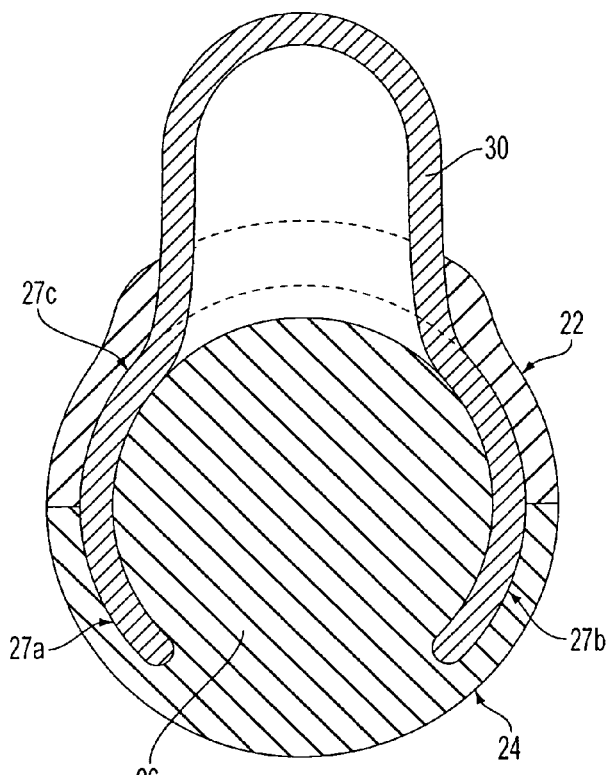
FIG. 4 is a cross-sectional view of the embodiment of FIG. 1 taken along line A—A of FIG. 1.

As shown in FIG. 4, the tapered blade holder 26 is secured to the lower body contour wall 24 distal end via a molded connection spanning approximately 90 degrees of the circumference of the generally circular cross section area of the tapered blade holder 26 at the point of attachment, allowing the guard 30 to effectively shield approximately 270 degrees about the axis of the blade when fully extended. FIG. 4 is a cross-sectional view of the embodiment of FIG. 1 taken along line A-A of FIG. 1, showing the point of attachment between the tapered blade holder 26 and the lower body contour wall 24, and the semicircular opening at the distal end of the body 20 through which the guard is extended and retracted during use. The cross section shown in FIG. 4 also shows the enlarged distal end of the guard 30, which is required to provide sufficient clearance for the blade when fully extended. This enlarged distal end is shown as one example, an may be modified to accommodate any blade type or guarding purpose.

In FIG. 4, the molded connection between the tapered blade holder 26 and the lower body contour wall 24 provides a first and second slot 27a and 27b on either side of the holder 26, for use in guiding the guard 30 between extended and retracted positions and preventing twisting or distortion. As additional support for the guard 30, the assembly of body contour walls 22 and 24 creates a third slot 27c between contour wall 22 and the tapered blade holder 26, linking slots 27a and 27b, such that a continuous semicircular slot is provided at the distal end, about the tapered blade holder 26, through which the guard 30 travels between fully extended and fully retracted positions. The guard 30, as described in greater detail below, has a generally semicircular cross section and is sized at a proximal end to extend and retract through the semicircular distal opening provided by the body 20, and is enlarged at a distal end to surround the blade 40 without interference when extended. The guard 30 can be constructed of any suitable material, including transparent or opaque polycarbonate materials. A transparent guard is advantageous in allowing the user to see the blade 40 even when it is fully shielded by the guard.

In the first embodiment of the present invention shown in FIG. 1, the guard 30 does not have a fully circular cross section at the distal end due to the molded attachment of the tapered blade holder 26 to the lower body contour wall 24. This feature ensures the user is allowed to firmly grip a surface that is singularly molded with the blade holder 26. This presents a more positive grip which is less susceptible to unwanted blade or gripping surface movements due to tolerances between the guard 30 and each body contour wall 22 and 24. The enlarged distal end of the guard 30 which remains external to the body 20 when fully retracted however, is rigid enough to provide additional control and blade orientation with one or more fingers of the user if so desired during use.

Figure 5A:
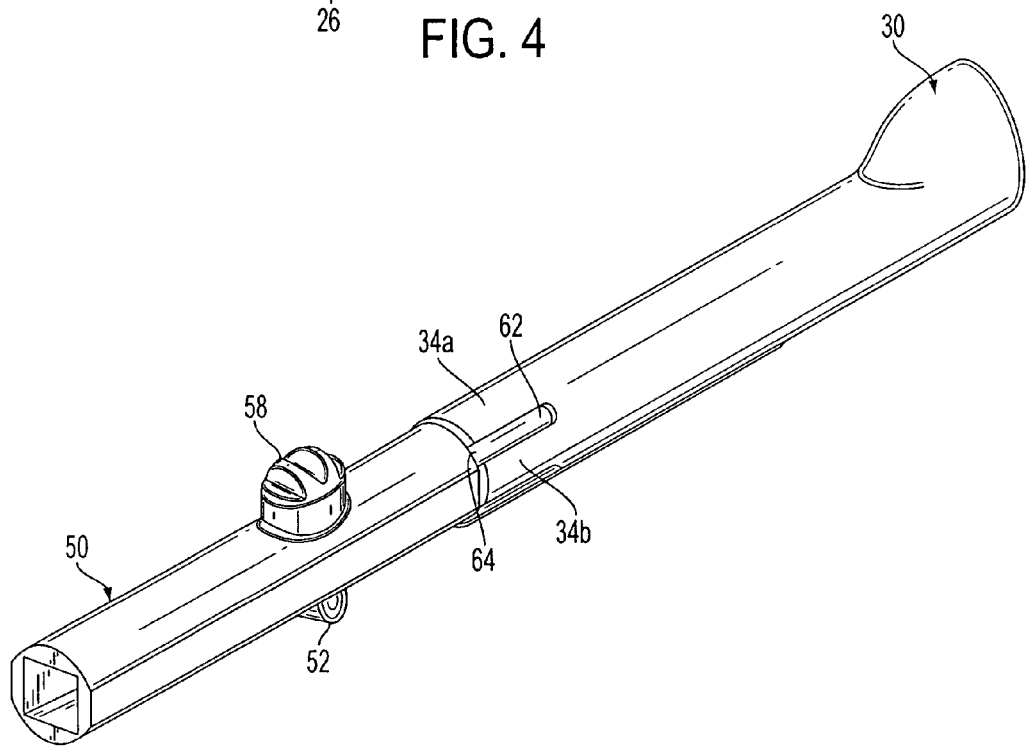
FIG. 5A is a perspective view of an embodiment of the engagement between the guard positioning mechanism and the guard in accordance with an embodiment of the present invention.
Figure 5B:
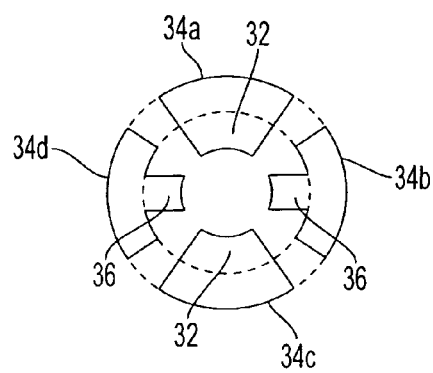
FIG. 5B is a cross-sectional view of the embodiment of the engagement end of the guard in FIG. 5A.
Figure 5C:
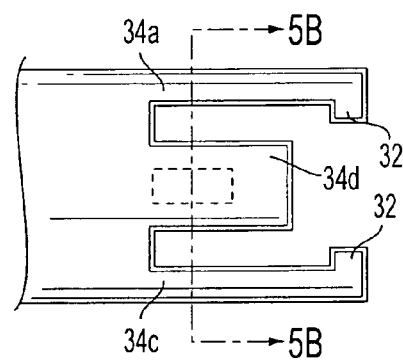
FIG. 5C is an elevational view of the embodiment of the engagement end of the guard in FIG. 5A.
Figure 5D:
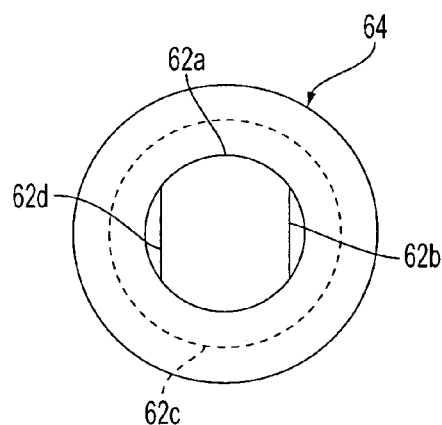
FIG. 5D is a cross-sectional view of the embodiment of the engagement end of the guard positioning mechanism in FIG. 5A.
Figure 5E:
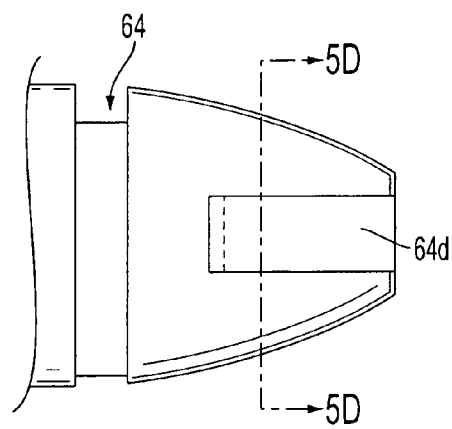
FIG. 5E is an elevational view of an embodiment of the engagement end of the guard positioning mechanism in FIG. 5A.
Figure 6:
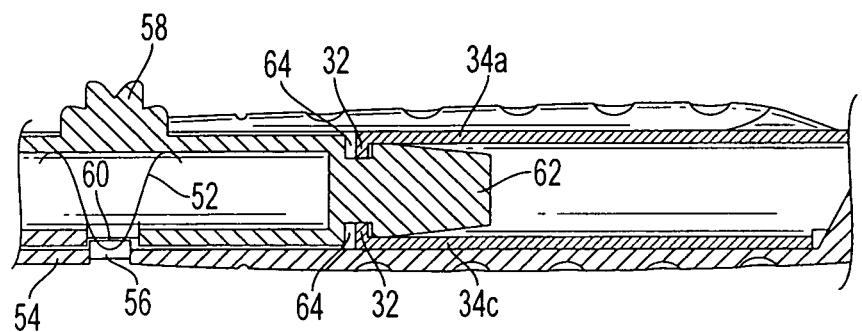
FIG. 6 is an enlarged cross-sectional view of the embodiment of the guard positioning mechanism and the guard of FIG. 5A taken along line B-B of FIG. 1.
Figure 7:
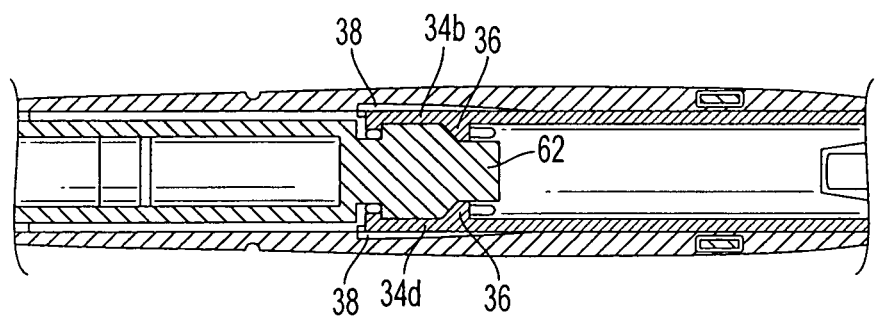
FIG. 7 is an enlarged cross-sectional view of the embodiment of the guard positioning mechanism and the guard of FIG. 5A taken along line C-C of FIG. 1.

FIGS. 5A-5E, 6 and 7 show additional details of the guard positioning mechanism 50, the guard 30, and the pushback prevention mechanism therebetween. FIG. 5A illustrates the engagement between the guard positioning mechanism and the guard, and FIGS. 6 and 7 illustrate an enlarged cross-sectional view of the engagement shown and described in relation to the body 20. FIGS. 5B-5E provide additional views of the engagement mechanisms of both the guard positioning mechanism and the guard.

As shown in FIG. 5A, the guard positioning mechanism 50 has a generally circular cross section and is sized to slidably fit within the hollow chamber within the body 20. The guard positioning mechanism 50 is mechanically engaged with the guard 30 to direct and control guard travel between a fully extended and fully retracted position. The combined length of the mechanism 50 and guard 30 is sufficient to allow a substantial portion of the guard 30 to retract within body 20. Only a partial radius of the enlarged distal end of the guard 30 remains exposed as shown in FIG. 1.

The guard positioning mechanism 50 is mechanically engaged with the guard 30 via a pushback prevention mechanism comprising a conical surface, or tapered locking pin, located at an engagement end of the guard positioning mechanism 50 and which is slidably positioned within a collet-like guard opening, described in greater detail below. The mechanical engagement between the positioning mechanism 50 and guard 30 allows the positioning mechanism 50 to control the slidable movement of the guard 30 between extended and retracted positions. External control of the guard positioning mechanism 50 is directed by the user via the raised protrusion 58 which extends from within the hollow chamber of the body 20 via channel 28. The ease of control allows the user one finger control of the positioning mechanism and the attached guard. The raised protrusion 58 can also be cantilevered to provide a user operable lock to further prevent undesired movement of the positioning mechanism 50, as described in greater detail below in reference to FIGS. 8G through 8L.

Figure 3C:
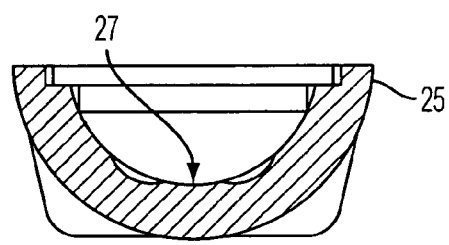
FIG. 3C is a cross-sectional view of the lower body contour wall of FIG. 3B illustrating a path between detent openings.

As shown in greater detail in FIG. 6, each position of the guard 30 is maintained by an engagement between a leaf spring 52, located within a body cavity of the guard positioning mechanism 50, and either a first or second detent 54 and 56 located in the lower body contour wall 24. The guard positioning mechanism 50 is substantially hollow and contains a leaf spring 52 which is oriented within the guard positioning mechanism 50 with an exposed spring apex extending from the guard positioning mechanism 50 via an opening 60. The spring apex extending from opening 60 firmly presses against the lower body contour wall 24 when sliding between extended and retracted positions. The lower body contour wall 24 includes a first and second detent 54 and 56, located at opposite positions within the substantially hollow chamber such that the leaf spring engages the first detent 54 when the guard positioning mechanism 50 is in a fully retracted position, and engages the second detent 56 when the guard positioning mechanism 50 is in a fully extended position. Slidable movement of the guard positioning mechanism 50 between positions through the use of a prevailing force is opposed with a slight resistance created by the leaf spring 52 contact with the lower body contour wall 24 between detents. As shown in greater detail in FIG. 3C, the path traveled by the leaf spring 52 between detents can also be provided as a flattened surface 27 on an inside radius of the lower body contour wall 25. To ensure consistent spring/wall contact, the surface 27 can be flattened (to lower the surface) or include one or more ribs (not shown) to raise the surface 27, such that the spring 52 maintains a constant deflection when moved between detent openings, regardless of changes in the contour wall 25. The slight resistance provided allows the guard 30 to maintain a position when the user releases the external control 58, and prevents the guard from freely sliding.

As shown in FIG. 5A, the guard 30 extends between a generally circular cross section at a proximal end, and a generally semicircular cross section at an enlarged distal end. The guard is not fully circular along its entire length due to the need to surround the molded attachment of the holder 26 and the blade 40, which is in rigid attachment to the body via the lower body contour wall 24. Therefore the guard 30 includes opposite engagement and shielding ends. At the engagement, or proximal end, the guard has a generally circular cross section and is sized to slidably fit within the hollow chamber within the body 20, and mechanically engage the guard positioning mechanism 50 which directs and controls the travel of the guard 30 between a fully extended and fully retracted position as described above. The engagement end of the guard 30 is described in greater detail below.

The shielding, or distal end of the guard 30 shown in FIG. 5A, has a generally semicircular cross section and is sized to extend and retract through the semicircular distal opening provided by the body 20. An enlarged semicircular area, as also shown in FIG. 4, is provided at the extreme end of the distal end of the guard 30 to provide adequate clearance of the blade 40 when the guard 30 is fully extended. Additionally, as noted above, the enlarged semicircular area provided at the extreme distal end of the guard 30 remains external to the body 20 when the guard is fully retracted, and is rigid enough to provide additional control and blade orientation with one or more fingers of the user if so desired.

As shown in FIGS. 5B and 5C, the engagement, or proximal end of the guard 30, includes a pushback prevention mechanism comprising a collet-like coupling mechanism having four flanges 34a, 34b, 34c and 34d, to engage the tapered locking pin 62 located at the engagement end of the guard positioning mechanism 50. As shown in FIGS. 5D and 5E, the engagement end of the guard positioning mechanism 50 includes a pushback prevention mechanism comprising a tapered locking pin 62 having four surface quadrants 62a, 62b, 62c, and 62d. The coupling mechanism of the guard 30 engages the four surface quadrants 62a, 62b, 62c, and 62d of the tapered locking pin 62 using the four flanges 34a, 34b, 34c and 34d extending from the engagement end of the guard and surrounding a mating opening for the locking pin 62. Flanges 34a and 34c are located on opposite sides of the mating opening and are used to engage surface quadrants 62a and 62c of locking pin 62 to achieve mechanical engagement. Flanges 34b and 34d are also located on opposite sides of the mating opening and are used to engage surface quadrants 62b and 62d of locking pin 62 to achieve pushback prevention engagement.

Mechanical engagement between guard positioning mechanism 50 and the guard 30 is shown in FIGS. 5A-5E and 6. FIG. 6 is an enlarged cross-sectional view showing the locked engagement between flanges 34a and 34c, and pin quadrants 62a and 62c. FIG. 7 is an enlarged cross-sectional view rotated 90 degrees relative to the view of FIG. 6, and showing the potential for engagement between flanges 34b and 34d, and pin quadrants 62b and 62d.

As shown in FIGS. 5 and 6, the locking pin 62 is inserted into the coupling mechanism of the guard 30 until locked into place by locking flanges 34a and 34c. To engage the guard 30 with the guard positioning mechanism 50, the locking pin 62 is inserted into the four locking flanges 34a, 34b, 34c and 34d extending from the body of the guard 30. The locking pin 62 is tapered along quadrants 62a and 62c, allowing an inner lip 32, located about the inside circumference of two locking flanges 34a and 34c, to displace the flanges outward until the inner lip 32 is disposed into the groove 64 near the base of the locking pin 62, locking the guard into place. When fully engaged, the inner lip 32 engages the groove 64 located about the outside circumference of the locking pin 62, preventing the separation of guard 30 and guard positioning mechanism 50. The two locking flanges 34a and 34c are made of a material sufficiently pliant to allow displacement outward due to the insertion of locking pin 62, yet maintain engagement between the inner lip 32 and groove 64 during movement of the guard positioning mechanism 50.

Pushback prevention engagement between guard positioning mechanism 50 and the guard 30 is shown in FIGS. 5A-5E and 7. When engaged and fully extended, additional movement of the guard 30 and guard positioning mechanism 50 toward one another will engage the pushback prevention mechanisms incorporated into the coupling mechanism components described above. Travel of the guard 30 toward a stationary guard positioning mechanism 50 indicates that a force, not properly originating from the user, is acting in a manner to retract the guard. Such forces can result from a number of causes, including external forces applied to the guard when fully extended. Examples include instances where the extended guard 30 is pushed, bumped or struck, or when the handle 10 is dropped on the end from which the guard 30 extends. Such forces could result in the guard partially retracting and exposing part or all of the blade 40. To prevent this, the pushback prevention mechanism is engaged when the guard 30 is fully extended and an external force is applied to the guard which would tend to force the guard from the fully extended position against the resistance of the guard positioning mechanism 50.

As shown in FIGS. 5A-5E and 7, the locking flanges 34b and 34d extending from the body of the guard 30 each include an inner ramp 36, which engages the surface quadrants 62b and 62d of the locking pin 62 of the guard positioning mechanism 50 when the guard 30 is moved towards the guard positioning mechanism beyond the locking point described above. Quadrants 62b and 62d include a slight flat along the taper of the pin such that in a normal, engaged position, the inner ramp contacts 36 do not displace the flanges 34b and 34d. However, while fully extended, if there is an external force applied to the guard 30, forcing the guard towards the guard positioning mechanism 50, the pin surface quadrants 62b and 62d engage the ramps 36 and the locking flanges 34b and 34d are displaced in an outward direction, against the inner walls of the hollow chamber within the body 20. As the flanges 34b and 34d are displaced, each contacts a groove 38, located along the inner wall of the chamber. The flanges 34b and 34d, once fully displaced within the groove 38, travel along the groove a minute distance until contacting a shoulder at the end of each groove, stopping any further travel of the flanges in a rearward direction, thus preventing any noticeable retracting movement of the guard 30 from the fully extended position.

Flanges 34a and 34c also work in cooperation to achieve the pushback prevention function. The groove 64 which is engaged by the inner lip 32 of flanges 34a and 34c, has a sufficient width to allow the inner lip to travel slightly rearward during engagement of the pushback prevention mechanism, such that the flanges 34a and 34c do not interfere with the function of the pushback prevention mechanism of flanges 34b and 34d. If the inner lip 32 were not allowed to travel in the groove 64, any rearward force on the guard 30 would displace the guard positioning mechanism 50 before the pushback prevention mechanism could engage.

Yet another cooperation feature between flanges 34a and 34c, and the pushback prevention mechanism can include an inner surface of flanges 34a and 34c each including a slight relief (not shown), which prevents the flanges from possibly displacing slightly outwards when inner lip 32 is engaged in the groove 64, due to flange thickness and the surface of pin 62. Likewise, flanges 34b and 34d are slightly shorter than flanges 34a and 34c, allowing the mechanical engagement to occur within the chamber housing without interference.

The resistance provided by the leaf spring 52 engagement with the fully extended detent slot 56 is sufficient to hold the guard positioning mechanism 50 in place when an external force is applied to the fully extended guard 30. The guard positioning mechanism 50 remains in position as the guard 30 is slightly displaced rearward activating the pushback prevention mechanism incorporated into the coupling mechanism as described above. In this embodiment, the slight rearward displacement prior to full activation of the pushback prevention mechanism is negligible.

In a second version of the first embodiment, the guard positioning mechanism 50 of the user actuator can be constructed with an integral cantilever beam spring along a bottom surface of the mechanism body to provide the spring biasing mechanism forcing detent engagement. In this version as shown in FIGS. 8A through 8F, the guard positioning mechanism 50 has an integral cantilever beam 70 along a bottom surface, secured at a first end and flexing at an opposite end, and upon which an inclined projection 72 is used to provide the spring biasing mechanism. This plastic molded spring can be used to replace the leaf spring 52 and maintain each position of the guard 30 by an engagement between the molded spring and the first or second detent 54 and 56 located in the lower body contour wall 24.

In this second version, the guard positioning mechanism 50 includes at least one inclined projection 72, wherein the incline (i.e., 45 degrees) is provided to allow easy entry and removal from the detents. The integral cantilever beam 70 firmly presses the projection 72 against the lower body contour wall 24 when sliding between extended and retracted positions. As noted above, the lower body contour wall 24 includes a first and second detent 54 and 56, located at opposite positions within the substantially hollow chamber such that the projection 72 engages the first detent 54 when the guard positioning mechanism 50 is in a fully retracted position, and engages the second detent 56 when the guard positioning mechanism 50 is in a fully extended position. Slidable movement of the guard positioning mechanism 50 between positions through the use of an applied force on the external control 58 is opposed by a slight resistance created by the projection 72 in contact with the lower body contour wall 24. The slight resistance provided allows the guard 30 to maintain a position when the user releases the external control 58, and prevents the guard from sliding freely.

When constructed having similar spring characteristics, the use of the integral cantilever beam 70 and the inclined projection 72 eliminates the need for a metal spring component. The spring biasing mechanism therefore becomes part of the user actuator (i.e., raised operator control 58 and guard positioning mechanism 50), and all can be made from one piece of material. This reduces variability in the "feel" when moving the guard positioning mechanism 50 between positions (i.e., in and out of detent engagements). In the above embodiments, when the metal leaf spring component 52 is assembled into the guard positioning mechanism 50, the dimensions of the metal spring component can be altered due to the nature of the assembly method required. Additionally, the metal leaf spring can have a reduced cycle life relative to the plastic molded spring, and can deform after few detent engagements.

Combining the spring biasing mechanism and the user actuator into one, thus eliminating one of the two parts, allows for tighter tolerances between the remaining components (i.e., detent and spring biasing mechanism). Furthermore, the variability incurred as part of the assembly method between the metal leaf spring component and the user actuator is also removed. The tighter tolerances and removal of the assembly method added variability ensures smooth and consistent detent engagement. As with the above embodiments, the smoother detent engagements also provide feedback to the user through an audible click and a mechanical snap that can be felt through the user actuator.

The integral cantilever beam 70 and inclined projection 72 can be modified in shape and form, and still act as the spring biasing mechanism. For example, in yet another version the cantilever spring 70 and inclined projection 72 can be molded into the lower body contour wall 24 (i.e. handle base) and the detents 54 and 56 placed into the guard positioning mechanism 50 of the user actuator, thereby reversing the locations of these two features.

The guard positioning mechanism 50 of the user actuator can also be constructed with an integral cantilever beam along a top surface of the mechanism body to provide an upwardly biased, user operable lock for engagement with a detent, groove, or slot 84 provided in the upper body contour wall 22.

Figure 8H:
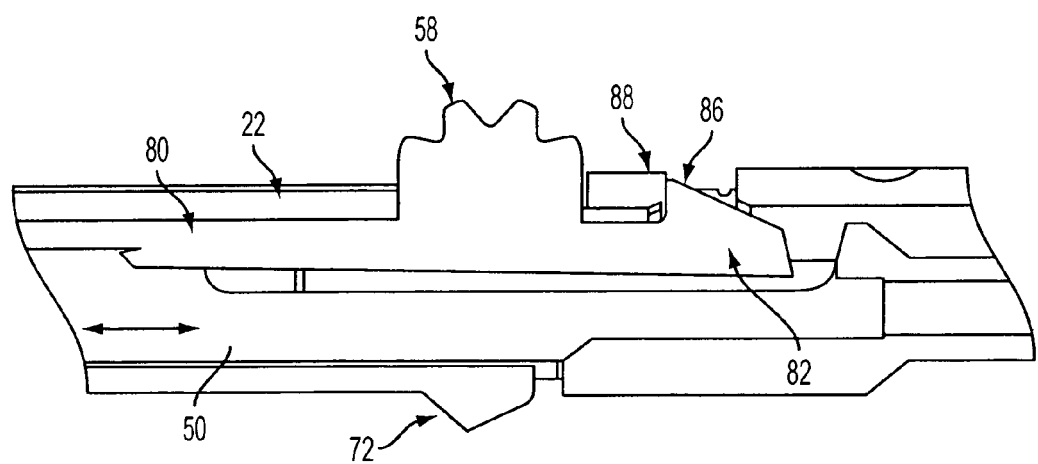
FIG. 8H is a cross-sectional view of the guard positioning mechanism and user operable lock of FIG. 8G in a locked position in accordance with an embodiment of the present invention.
Figure 8I:
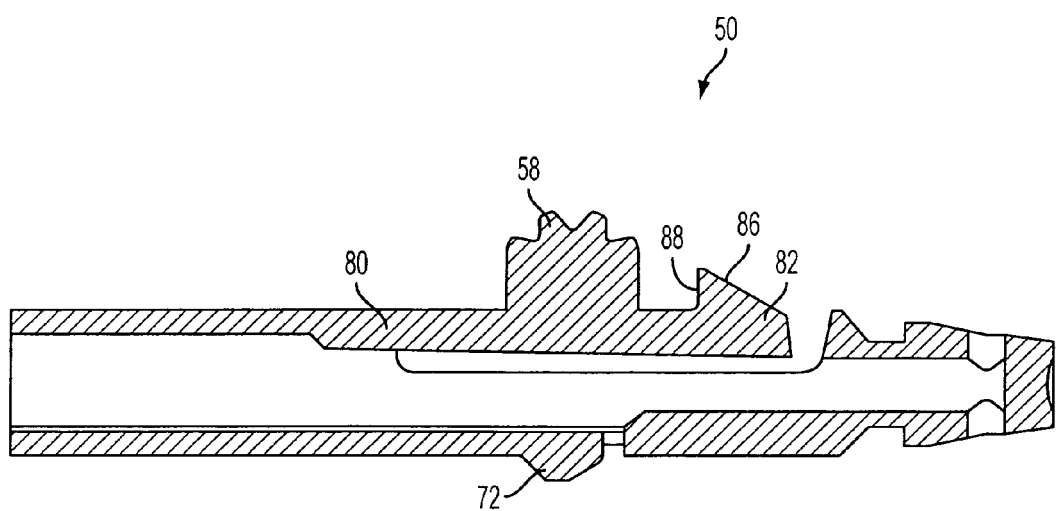
FIG. 8I is a cross-sectional view of the guard positioning mechanism and user operable lock of FIG. 8G.
Figure 8J:
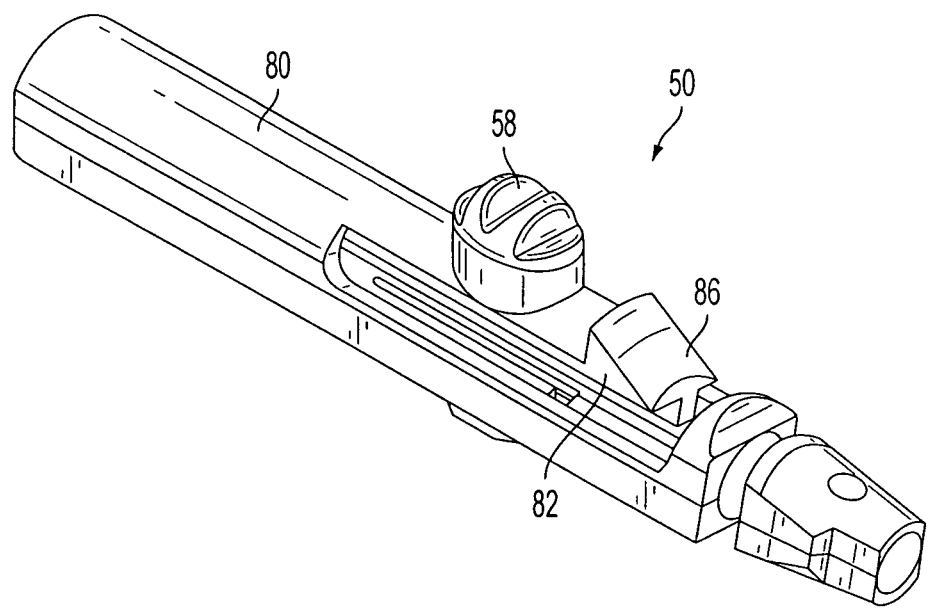
FIG. 8J is a perspective view of the guard positioning mechanism and user operable lock of FIG. 8G.
Figure 8K:
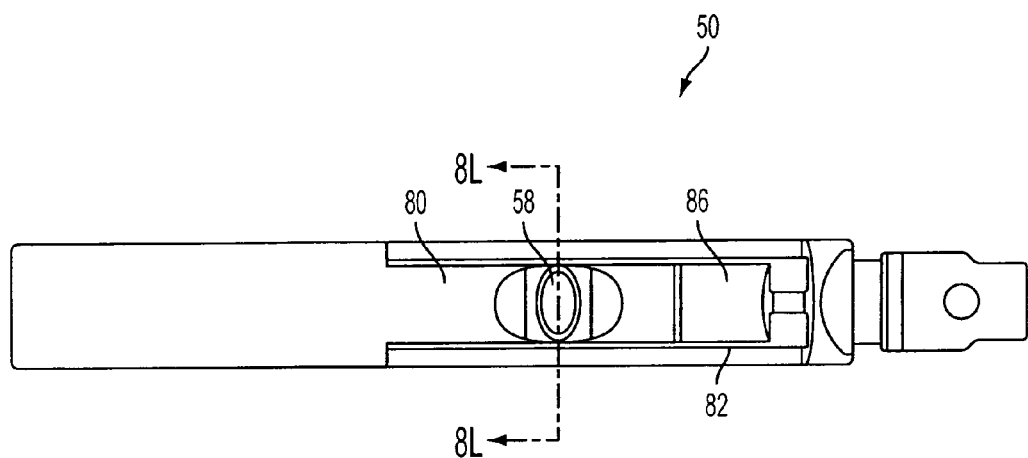
FIG. 8K is a top view of the guard positioning mechanism and user operable lock of FIG. 8G.
Figure 8L:
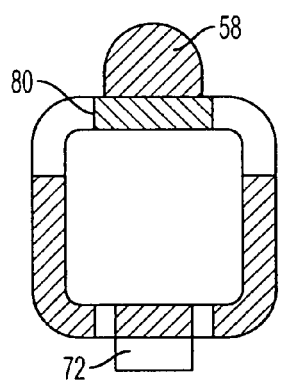
FIG. 8L is a cross-sectional view of the guard positioning mechanism and user operable lock of FIG. 8G.

FIG. 8G is an exploded perspective view of another embodiment of the present invention including such a user operable lock. In this embodiment, as shown in FIGS. 8G through 8L, the guard positioning mechanism 50 has an integral cantilever beam 80, secured at a first end and flexing at an opposite end upon which an inclined projection 82 is used to provide the upwardly biased, user operable lock mechanism. FIG. 8H is a side cross-sectional view of the guard positioning mechanism and additional user operable lock in a locked position. FIGS. 8I through 8L are views of the guard positioning mechanism and additional user operable lock of FIG. 8G. Specifically, FIG. 8I is a cross-sectional view of the guard positioning mechanism 50 and user operable lock, and FIG. 8J is a perspective view of the guard positioning mechanism 50 and user operable lock. FIG. 8K is a top view of the guard positioning mechanism 50 and user operable lock, and FIG. 8L is a cross-sectional view taken along line 8L of FIG. 8K. In this embodiment, the plastic molded beam 80 can be used to engage the inclined projection 82 with the slot 84, and maintain the forward, or extended position of the guard positioning mechanism 50 until released by the user. In doing so, the shield can be substantially protected from becoming accidentally displaced during shipping or during mishandling when packaged and exposing the blade.

In this embodiment, the guard positioning mechanism 50 includes at least one inclined projection 82, wherein the incline or sloped wall 86 (i.e., 30 degrees from the horizontal) is provided to allow easy entry into the slot 84. The perpendicular or vertical wall 88 of the inclined projection 82 is provided to engage a surface of slot 84, preventing rearward motion of the positioning mechanism 50 until a user depresses the raised operator control 58 which is now disposed on the integral cantilever beam 80, thereby forcing the integral cantilever beam 80 downward and disengaging the inclined projection 82 from the slot 84. Once disengaged, the user can retract the positioning mechanism 50 and guard 30. To activate the user operable lock mechanism, the user advances the positioning mechanism 50 and guard 30, which also serves to advance the integral cantilever beam 80 and the inclined projection 82. The leading or sloped edge 86 increasingly loads and deflects the integral cantilever beam 80 when contacting the upper body contour wall 22 until the positioning mechanism 50 is in the proper position for the inclined projection 82 to "snap" into place in the slot 84. Although the upper body contour wall 22 is shown in this example having a slot, any recess, cavity, notch, opening or other structure sufficient to capture and release the inclined projection 82 can be used.

The integral cantilever beam 80 firmly presses the projection 82 against the upper body contour wall 22 when sliding the positioning mechanism 50 near the fully extended position. In this version, the upper body contour wall 22 includes the slot 84, such that the projection 82 engages the slot 84 when the guard positioning mechanism 50 is in a fully extended position. Slidable rearward movement of the guard positioning mechanism 50 is then opposed by the projection 82 in contact with the slot 84 of the upper body contour wall 22. This locked position allows the guard positioning mechanism 50 to maintain its position even in cases where the device is struck at the proximal end, rather than being struck at the distal, or guarded end. Although the embodiment shown in FIGS. 8G through 8L has the integral cantilever beam 80 extending toward the distal end of the device, the slot 84 can be disposed at any number of positions such as toward the proximal end of the device, and the beam and/or projection can therefore, also be provided extending toward the proximal end of the device, or anywhere along the sides of the positioning mechanism 50.

As noted above, the pushback prevention mechanism of FIGS. 5A through 5E, 6 and 7, substantially prevents rearward movement of the fully extended guard 30 when struck, bumped or contacted in any way at the distal end of the device. Further, the user operable lock mechanism substantially prevents the shield from becoming accidentally displaced during shipping or during mishandling when packaged. However, when struck at the proximal end of the device, the mass of the positioning mechanism 50 can in some cases, force the positioning mechanism 50 rearward due to inertia. In/this case, the pushback prevention mechanism may not engage, as the pushback prevention mechanism functions most effectively when the guard 30 is struck, bumped or contacted and is forced rearward toward the stationary positioning mechanism 50. If the positioning mechanism 50 is itself moving rearward, as can be the case when the device or its package is struck at the proximal end, the pushback prevention mechanism alone may not sufficiently maintain the guard 30 in a fully extended position. However, when the positioning mechanism 50 is provided with the user operable lock as described above, a degree of redundancy is designed into the device. This eliminates the undesired movements of the positioning mechanism 50, as the user operable lock incorporates a positive catch that provides maximum holding force along the long axis of the device. The locking contact surface between projection 82 and the slot 84 is provided at a substantially 90° angle relative to the force vector imposed during a proximal end impact.

Undesired movement of the positioning mechanism 50 can be further prevented through packaging techniques. For example, the device can be rotated and packaged in a "tray" or fitted package, such that the positioning mechanism 50 is prevented from moving by the package itself. The package can also be constructed using clear "blister pack" technology or include a band around the handle of the device, which tightly contacts the device. This contact, specifically contact between packaging and the raised operator control 58, blocks any movement of the control 58, thereby preventing movement of the positioning mechanism 50. The device can also be positioned within the package such that the proximal end of the device is near the package end having the largest area of material (i.e., opposite the end to be opened). This additional material, or added padding, can act as a cushion for the proximal end of the device when the package is struck or bumped. Still other packaging techniques can include shipping the device unguarded, foam packaging the unguarded device, and/or including labeling to note that drops or abnormal uses/shocks can impair the safety of the device.

As noted above, the undesired movement of the positioning mechanism 50 can be prevented through design techniques. For example, returning to FIG. 3A, the undesired movement of the positioning mechanism 50 can be substantially prevented through the engagement between the spring 52, located within a body cavity of the guard positioning mechanism 50, and the first and second detent 54 and 56 located in the lower body contour wall 24. Similarly in FIG. 8A, the undesired movement of the positioning mechanism 50 can be substantially prevented through the engagement between the integral cantilever beam 70 and inclined projection 72, and the first and second detent 54 and 56 located in the lower body contour wall 24. In each case, when kept in a position, such as in a guarded position, the components can take a "set" in that position to further prevent movement of the guard positioning mechanism 50. Where further protection from undesired movement is required, the user operable lock can be provided. In that case, the undesired movement of the positioning mechanism 50 can be substantially prevented through the engagement between the integral cantilever beam 80 and inclined projection 82, and the slot 84 located in the upper body contour wall 22.

In yet another technique in which undesired movement of the positioning mechanism 50 can be prevented, a "flaring lock", such as that provided by the pushback prevention mechanism described above in connection with FIGS. 5A through 5E, 6 and 7, can be inverted and provided on the positioning mechanism 50. When the user slides the raised operator control 58, the movement collapses a number of flared elements (which are biased outward in a relaxed position to secure the positioning mechanism 50), thereby releasing the positioning mechanism 50 for movement.

Figure 13A:
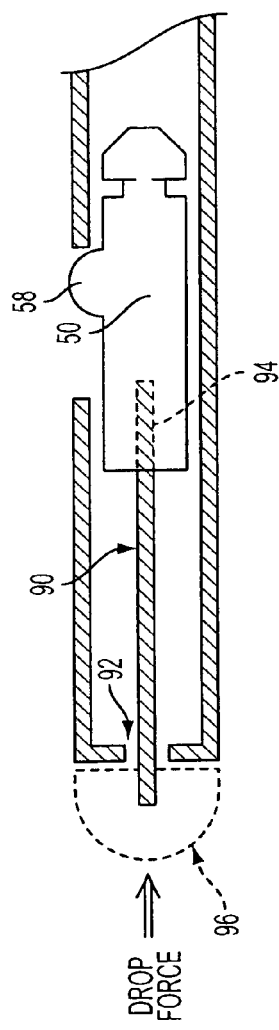
FIG. 13A is a cross-sectional view of another embodiment of the present invention with a drop-force operable lock.

In still another technique in which undesired movement of the positioning mechanism 50 can be prevented, a shock absorbing tip can be provided on the end of the device (i.e., a rubber bumper), or provided on the end of a pin or rod, as described in greater detail below with reference to FIG. 13A.

Figure 13B:
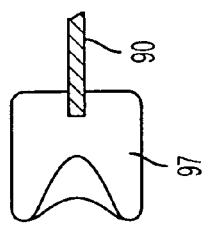
FIG. 13B is a view of an alternate contact button shape for the embodiment of FIG. 13A.
Figure 13C:
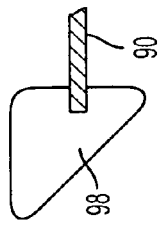
FIG. 13C is a view of another alternate contact button shape for the embodiment of FIG. 13A.

In another embodiment of the present invention, a drop-force operable lock can be provided to substantially prevent the guard from becoming accidentally displaced and exposing the blade when a force is applied to the proximal end of the device. In a shock absorbing technique, a pin or rod can be attached to the positioning mechanism 50 and protrude out the base, or proximal end of the device as shown in FIG. 13A. FIG. 13A is a cross-sectional view of another embodiment of the present invention with a drop-force operable lock. In FIG. 13A, a pin 90 is provided through an opening 92, and is flush with the proximal end when the guard 30 is forward, and extends beyond the proximal end when the guard 30 is retracted. Should the proximal end of the device be struck or bumped when the guard is forward, the pin or rod transmits the impact force to the positioning mechanism 50 to maintain the positioning mechanism 50 and the guard 30 in an extended position. The pin or rod 90 contacts the back of the positioning mechanism 50 via a fitting 94, such as a threaded fitting, and can move an equal length to guard travel. In such a configuration, when the guard 30 is retracted, the pin 90 is in the "out" position, and when the guard 30 is extended and locked, the pin 90 is in the "in" position. A shock absorbing tip 96 can be provided on the end of the pin 90, and can have any number of shapes, such as tips 97 and 98 shown in FIGS. 13B and 13C, respectively. The tip can be made of a rubber eraser-like material added to proximal end of the device handle, and can be angled, similar to the rubber tips found on the proximal end of a toothbrush.

In yet another technique to prevent undesired movement of the positioning mechanism 50, a compression spring can be added to bias load forward during sudden movement, such as when the device is dropped. In still another technique to prevent undesired movement of the positioning mechanism 50, a rubber grommet can be provided about the positioning mechanism 50 to engage an inner surface of the device and stabilize the mechanism and resist movement.

In still another technique to prevent undesired movement of the positioning mechanism 50, a mechanical fuse can be provided to disable the device if the device is dropped. A twist lock feature can also be added to the positioning mechanism 50, such that a movement of the positioning mechanism 50 would require a forward force, as well as a force to one side (i.e., an "L"-shaped or twist movement). This may require changes to the positioning mechanism 50, guard 30 and base. An O-ring can also be provided as a stop and/or shock absorber for the positioning mechanism 50.

In still another technique to prevent undesired movement of the positioning mechanism 50, the spring 52 or inclined projection 72 can be modified to include a vertical wall in addition to the contour (in the case of the spring 52) and the angles (typically 30° to 45° in the case of the inclined projection 72). Therefore, to release the newly added vertical wall of the spring 52 or inclined projection 72 from the first or second detent 54 and 56 located in the lower body contour wall 24, the user would be required to press against the spring 52 or inclined projection 72 in an upward motion with a finger from the base, raising the spring 52 or inclined projection 72 into the contoured or angled section. The user could then pull back on the positioning mechanism 50 as normal.

In still another technique to prevent undesired movement of the positioning mechanism 50, the engagement between the positioning mechanism 50 and the guard (i.e., the pushback prevention mechanism), can be provided with a degree of clearance or free movement, to allow the positioning mechanism 50 to move during an impact, but not pull the guard 30. Care is required to ensure that the additional movement space does not prevent the shield tabs to miss the detents in the handle halves (i.e., the function of the pushback prevention mechanism). This can possibly be overcome by adding mass to the guard, such as a weight (i.e., ball bearing), thereby making the shield tabs flare earlier during an impact or fall.

Figure 9A:
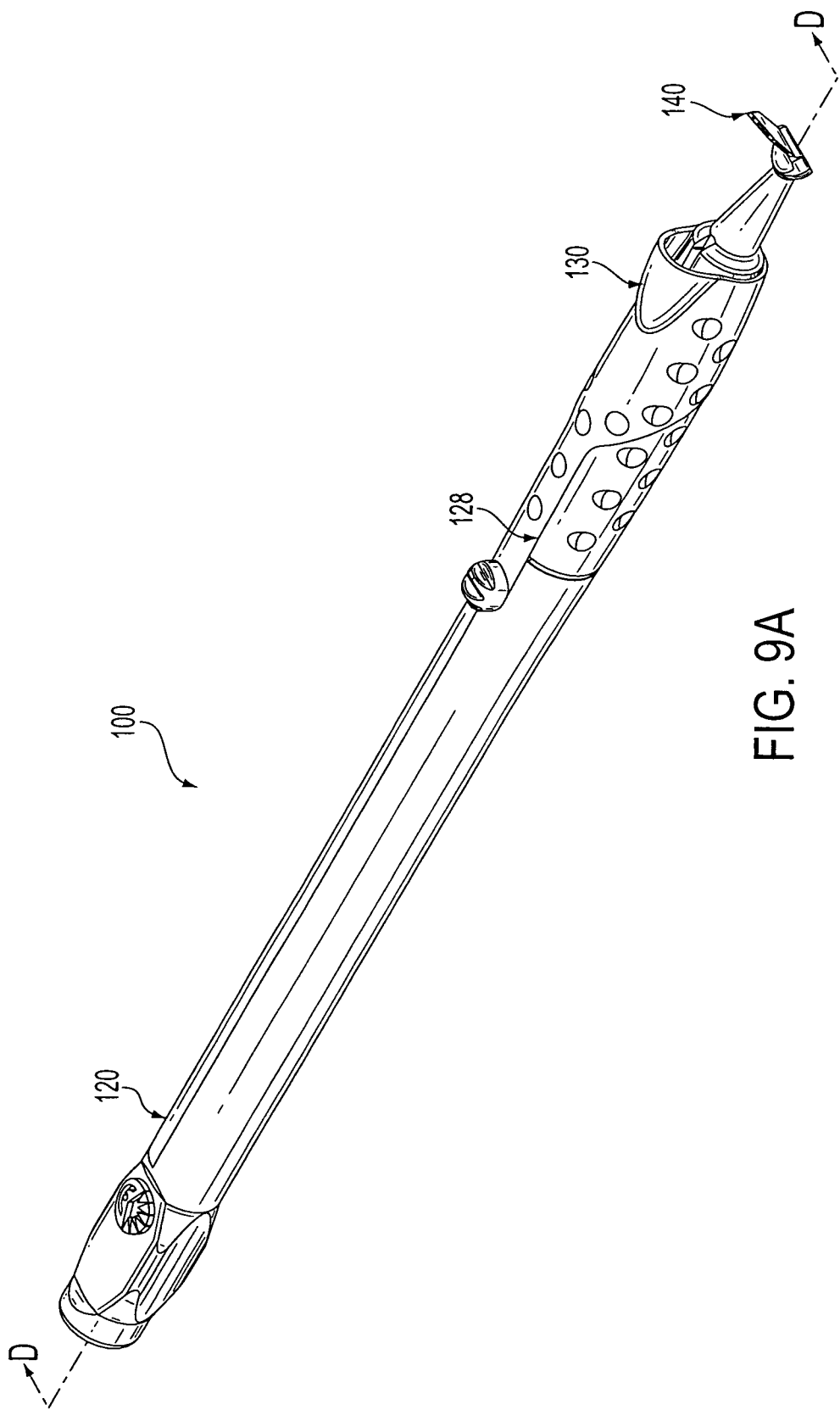
FIG. 9A is a perspective view of another embodiment of the present invention with the guard in a retracted position to expose the blade.

In still another embodiment, a fully circular guard may also be used to shield the exposed blade. In another embodiment of the present invention, the guard is fully circular at the distal end, which allows a larger portion of the guard to remain exposed when fully retracted. FIG. 9A is a perspective view of an embodiment of the present invention 100 with the guard 130 in a retracted position to expose a blade 140 for use. The guard 130, when in the retracted position, forms a smooth, uninterrupted handle surface between distal and proximal ends substantially as described in the first embodiment. When not in use, the guard 130 can be extended, as shown in FIG. 9B, to safely shield the blade 140.

Figure 10:
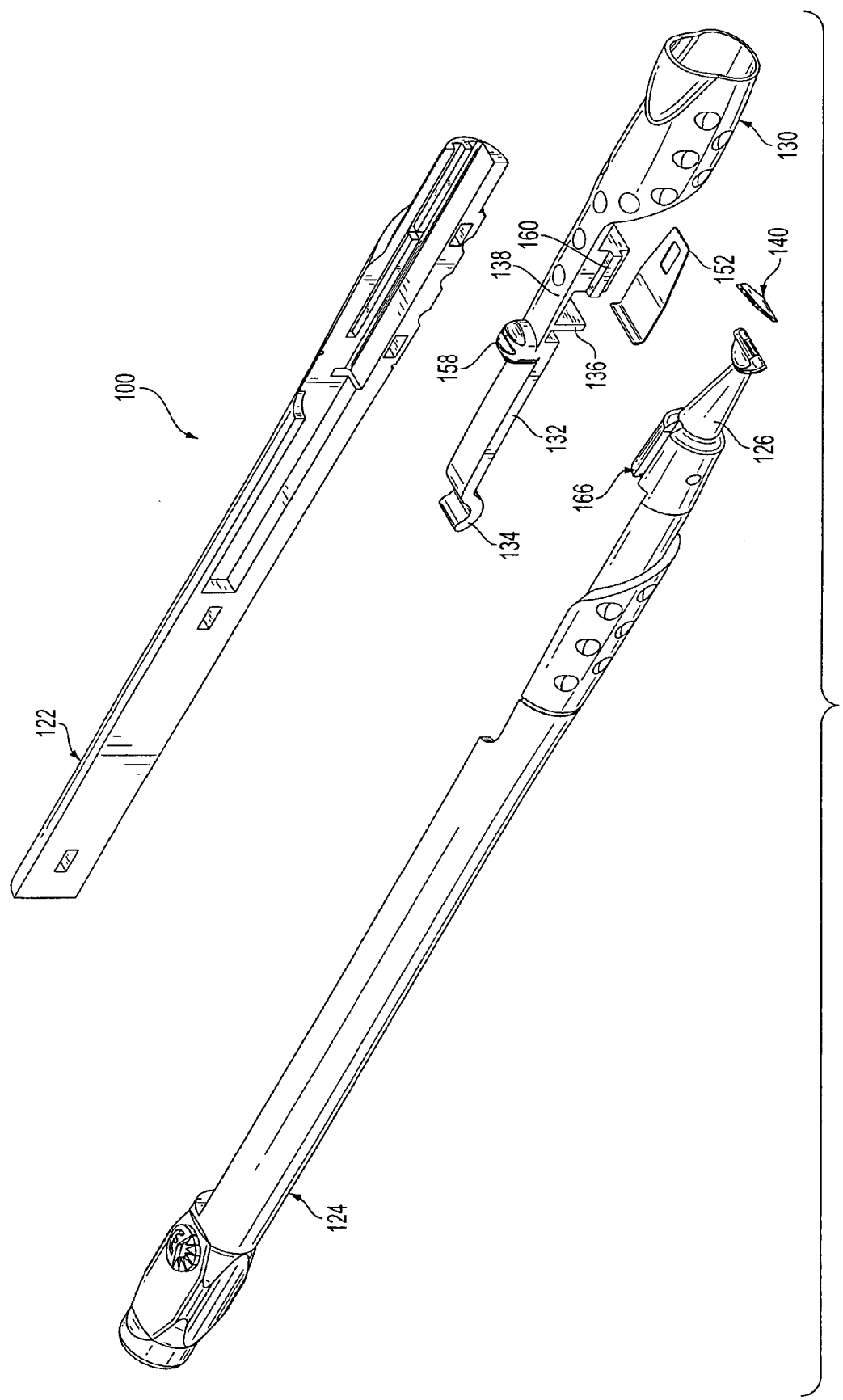
FIG. 10 is an exploded perspective view of the embodiment of FIG. 9A.

FIG. 10 is an exploded perspective view of the embodiment of FIG. 9A. The view of FIG. 10 includes a first and second body contour wall 122 and 124, formed to assemble as a handle body 120 and define a substantially hollow chamber within the body 120 to house a concealable portion of the guard 130. The first and second body contour walls 122 and 124 each provide a recess, which when assembled, creates a slot 128 extending rearward from the distal end and accessing the chamber to allow protrusion of a raised operator control 158 for the guard 130. The distal end of the first and second body contour wall 122 and 124 also includes an outer surface having a dimpled texture, extending from the distal end to a point slightly before the midpoint of the access slot 128. Additionally, as shown FIGS. 9A and 9B, the outer circumference surface area of an exposed portion of guard 130 also includes a dimpled texture, such that when fully retracted, the dimpled texture surface area is unbroken about the distal end of the body 120.

The distal ends of both the first and second body contour wall 122 and 124 further include a reduced outside diameter for receiving the exposed portion of guard 130. Specifically, as the guard 130 is slidably retracted, the fully circular exposed portion of guard 130 is received by the reduced outside diameter of the first and second body contour wall 122 and 124, until reaching a shoulder at the fully retracted position. Seating the guard 130 against the shoulder of the reduced outside diameter forms the smooth, uninterrupted handle surface between distal and proximal ends described above.

Figure 11:
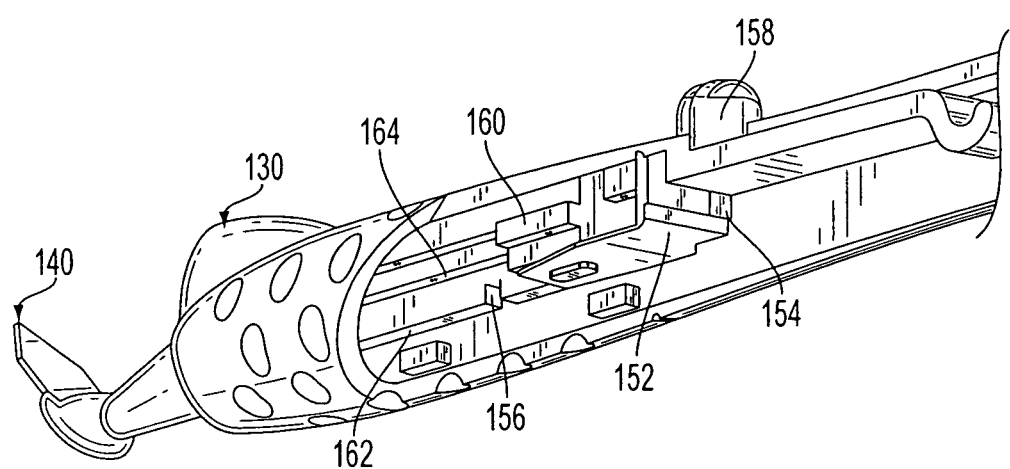
FIG. 11 is an enlarged cross-sectional view of the embodiment of FIG. 9A taken along line D-D of FIG. 9A.

In the embodiment of FIG. 10, the guard 130 is controlled to travel between a fully extended and fully retracted position via an external protrusion 158 accessed through channel 128 in a manner substantially as described in the embodiment of FIG. 3A. As shown in FIGS. 10 and 11, each position is maintained by an engagement between a spring 152 within a body cavity of the guard positioning mechanism 50 and either a first or second slot 154 and 156, provided along rails at either side of the hollow chamber within the body 120. The chamber, slots and rails are formed as described below, and serve to provide a slidable engagement surface for the guard to travel between fully extended and fully retracted positions.

As shown in FIGS. 10 and 11, the first and second body contour wall 122 and 124 assemble to define a substantially hollow chamber within the body 120 to house the guard 130 which contains a spring 152 mounted beneath a saddle 160 that is driven between rails on either side of the chamber. The guard 130 includes a fully circular distal end, provided to shield the blade 140 when fully extended. An elongated member 132 extends rearward from the fully circular distal end, and provides a platform supporting a saddle 160, a plate 136, an external protrusion 158 and a contoured end 134.

As shown in FIG. 11, each body contour 122 and 124 provides a first and second rail 162 and 164, along the inner wall of the chamber. The first rail 162 is provided to engage the spring 152, as described in greater detail below. The second rail 164 is provided to engage the saddle 160, and maintain saddle alignment between fully extended and retracted guard positions.

The first rail 162 is provided between saddle 160 and spring 152. The spring 152 is mechanically attached to the bottom of the saddle 160 and includes an extension having a 90 degree angle oriented to firmly press against the upper surface of the first rail 162 when sliding between extended and retracted positions. The upper surface of the first rail 162 of each contour wall 122 and 124 includes a first and second slot 154 and 156, located at opposite positions along the substantially hollow chamber such that the spring 152 engages the first slot 154 when the guard 130 is in a fully retracted position, and engages the second slot 156 when the guard is in a fully extended position. Slidable movement of the guard 130 between positions is opposed with a slight resistance created by the spring 152 contact with the rail surface on either side of the chamber. Additional features can be provided to prevent possible twisting of the fully circular distal end of the guard 130 when fully extended. As shown in FIG. 10, the second body contour wall 124 can include a recessed groove 166 extending along the surface of the distal end beneath the elongated member 132. A plate (not shown), extending below the elongated member, can be used to slidably engage the recessed groove 166 of wall 124, providing alignment and support for the elongated member 132 and the fully circular distal end of the guard 130 when traveling between fully extended and fully retracted positions.

Once the spring 152 engages either the first or second slot, the guard 130 is locked in place. To disengage the spring 152 requires the user to apply slight perpendicular pressure to the external protrusion 158 until the spring 152 is disengaged from the slot, and thereafter, a parallel force can be used to slidably move the guard 130 to a new position. As noted above, the spring 152 is oriented to firmly press against the surface of the first rail when sliding between extended and retracted positions, and maintain a position in the first or second slot when at extended or retracted positions. Therefore, to allow the application of slight perpendicular pressure required to disengage the spring 152 from either slot 154 or 156, the guard 130 includes the elongated member 132 extending into the chamber and contacting a surface via a contoured end 134. The guard 130 also includes a slight notch 138 at a point between the saddle 160 and a plate 136 extending downward and contacting the spring 152.

To disengage the spring 152 from either slot 154 or 156, a slight perpendicular pressure applied to the external protrusion 158 is transferred to the elongated member 132. The contact at the contour 134, and the slight notch at 138, allows the perpendicular pressure to displace the plate 136 downward, forcing the spring 152 from the slot. The plate 136 is slightly narrower than the spring 152, therefore the plate can freely move between rails and deflect the wider spring 152 from contact with rail 162. As with the embodiment of FIG. 3A, the protrusion 158 can provide simple and safe one finger control of the guard 130. Further, a user operable lock and a drop-force operable lock can be provided with the embodiment of FIG. 10 to prevent accidental retraction of the guard from the fully extended and guarded position in substantially the same manner as described above.

In a modified version of the embodiment of FIG. 10 (not shown), the first and second body contour wall assemble to define a substantially hollow chamber within the body to house the guard which contains a spring mounted beneath a saddle that is driven between rails on either side of the chamber substantially as described above. However, in this version, the spring is oriented to contact the bottom of the chamber and firmly press the saddle against the surface of at least one rail provided when sliding between extended and retracted positions. Each contour wall includes a first and second slot, located at opposite positions along at least one rail within the substantially hollow chamber such that the saddle, under pressure from the spring, engages the first slot when the guard is in a fully retracted position, and engages the second slot when the guard is in a fully extended position. Once the saddle engages either the first or second slot, the guard is locked in place. To disengage the saddle requires the user to apply slight perpendicular pressure to the external protrusion until the saddle is disengaged from the slot, and thereafter, a parallel force can be used to slidably move the guard to a new position.

Figure 12A:
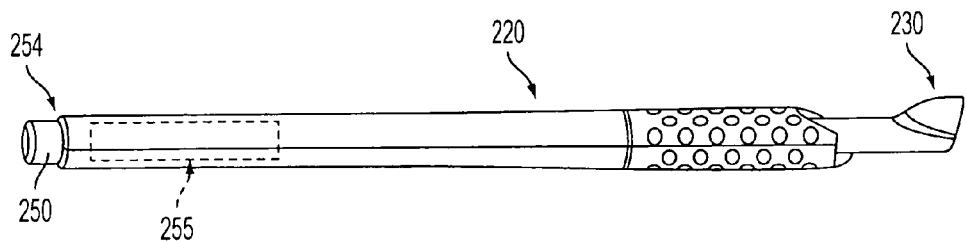
FIG. 12A is a perspective view of another embodiment of the present invention with a plunger type operator control and the guard in an extended position to shield the blade.
Figure 12B:
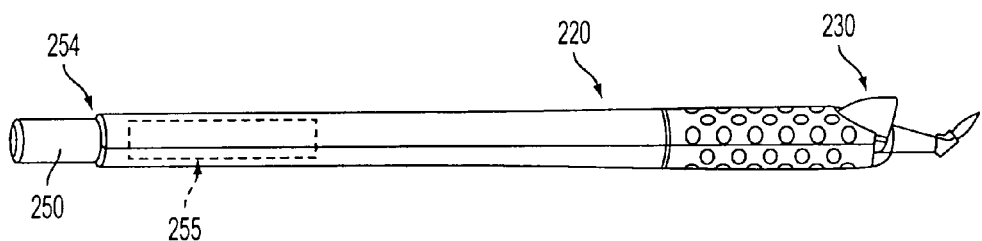
FIG. 12B is a perspective view of the embodiment of FIG. 12A with a plunger type operator control and the guard in a retracted position to expose the blade.

In another embodiment of the present invention, the slidable movement of the guard positioning mechanism is achieved using a plunger mechanism, as often associated with any of several ballpoint pen mechanisms that advances a pen tip through the push of a button. FIGS. 12A and 12B are perspective views of an embodiment of the present invention with a plunger type operator control and the guard in an extended and retracted position, respectively. Such mechanisms 255 typically involve a user activated plunger to advance a pen tip outward or to retract a pen tip inward in a longitudinal direction. The use of a pen mechanism at the proximal end of the device can provide an alternative to the side slot described in regards to the above embodiments. This would allow further variations in the single handed use of the embodiments described above.

Figure 12C:
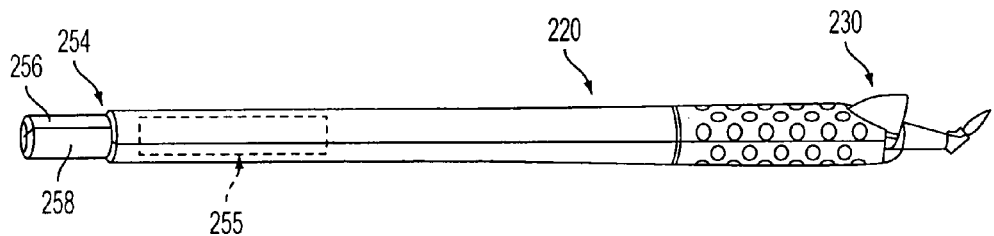
FIG. 12C is a perspective view of another embodiment of the present invention with a segmented plunger type operator control and the guard in a retracted position to expose the blade.

Such a pen mechanism would preferably utilize features similar to those in current pens to move the blade guard back and forth, as opposed to extending and retracting a pen tip. A user actuator can be located on the proximal end of the device that functions like a pen mechanism, i.e. to click the guard 230 in or out. Specifically, the mechanism could include a simple, single cylindrical member 250 extending from the proximal end opening 254 along the axis of the device body 220, and operate in a click-in and click-out fashion with an extension/retraction mechanism 255 as known to those skilled in the art. Alternatively, the mechanism could include a cylindrical member extending from the proximal end along the axis of the device and being divided into two or more members, or segments, 256 and 258 as shown in FIG. 12C. The divided members, when together, form the single cylindrical member; however each member can move relative to the others and provide an action unique to the movement of the particular divided member. Related divided function mechanisms can be found in multi-colored ballpoint pen mechanisms, which include different push button segments to extend different colors of pen tips from a single device.

In this example, various guards could be fabricated to fit inside and/or outside the body and/or chamber of the handle and still achieve the desired coverage of the blade. By disposing the guard partially inside and/or outside the device, the handle or body of the device can be constructed with a smaller diameter, or allow for the guard to better shield the blades described above or other blade geometry.

The guards could further comprise various shapes which can provide blade shielding at various places or of various strengths. Specifically, different guard shapes may provide different strength characteristics, and further allow the guard to withstand higher forces. These may also allow for a smaller guard, or enlarged guard distal end, thereby minimizing visual interference with the blade while providing maximum protection from blade contact resulting in a blade stick. Such a guard design can be either completely inside, outside or a combination of both, and the guard and enlarged guard distal end can be either open or closed, and can achieve full-circumference protection or provide alternative means to shield a blade depending on blade design. In examples which provide a semi-circular guard, the guard and enlarged guard distal end can still include other shapes, such as, but not limited to, triangle, square and/or box shapes, and still other shapes having multiple facets or sides, all with or without a circular or radius cross section, but which still provide shielding for blades of different geometries.

Returning to FIGS. 12A and 12B, the spring biasing mechanism that provides detent engagement within such a pen mechanism can include any number of configurations, such as the leaf spring and a cantilever beam described above, or a compression/extension spring. In still another example, the spring, such as the leaf spring, could be replaced with another spring biasing mechanism forcing detent engagement. In each example, the spring could provide a sufficient resistive force necessary for the guard function. In the embodiments of the present invention described above, the guard and enlarged guard distal end can be configured to withstand forces up to 3 lbs. in one example. Where such a spring biasing mechanism is used, the required applied force would typically be equal to or greater than the force which the guard can withstand. In yet another example, the spring biasing mechanism may be used to reduce the force required to move the guard back and forth, or to strengthen the guard design in each embodiment described above.

Unlike prior blade shielding mechanisms, embodiments of the present invention can withstand an inadvertent force. Such protection can be provided by utilizing a leaf spring or beam and detents to fix the guard in the extended and retracted position, by utilizing a pushback prevention mechanism and a user operable lock to prevent accidental retraction from the fully extended position, and by utilizing a drop-force operable lock to transfer any drop-force to the guard to prevent guard movement. These embodiments do not disengage or allow the guard to move from the shielding state to the non-shielding state by any reasonable inadvertent force applied longitudinally to the guard. Each embodiment therefore is able to implement a lock-out feature.

Embodiments of the present invention can be constructed of any suitable material, including a number of materials which can be autoclaved for repeated use. For example, where the embodiments are provided with metal blades and suitable body materials, multiple uses are possible using steam autoclave processes. In such examples, a preferred blade 40 and spring 52 material includes stainless steel (for metal spring versions only), and the body 20 and guard positioning mechanism 50 can be constructed of polyetherimide. The guard 30 can be constructed of transparent or opaque polycarbonate. Where the leaf spring 52 is omitted and replaced with an integral cantilever beam 70 and inclined projection 72, the beam and projection can also be constructed of a polyetherimide. Additionally, where the user operable lock is provided, the integral cantilever beam 80 and inclined projection 82 can also be constructed of a polyetherimide. The drop-force operable lock can be constructed of any rigid rod 90 and resilient rubber-like material for the tip 96.

Other blade materials can also be used, including silicon and diamonds, and the body 20 can be constructed of autoclave intolerant materials, such as high impact polystyrene. The use of high impact polystyrene will result in the substantial destruction of the device when autoclaved, thereby preventing reuse. In such applications, the leaf spring 52 can be constructed of stainless steel (for metal spring versions only), and the guard positioning mechanism 50 and guard 30 can be constructed of polyetherimide and polycarbonate, respectively.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

What is claimed is:

1. A surgical knife safety handle, comprising:
   a handle body having a longitudinal axis, at least one slot extending along a portion of said longitudinal axis and at least one detent adjacent to said slot;
   a knife holder for carrying a knife blade at a distal end of said handle body;
   a guard having an enlarged distal end to facilitate user contact with said enlarged distal end for handle orientation and control,
   wherein said guard is configured to at least partially enclose a knife blade carried by said knife holder, at least one of said knife holder and said guard being longitudinally moveable with respect to said handle body, wherein said detent releasably secures said at least one of said knife holder and said guard at a position with respect to said handle body; and
   a positioning mechanism for allowing a user to longitudinally move said at least one of said knife holder and said guard to selectively expose or cover said knife blade and having a user control mechanism disposed upon a cantilever, wherein said cantilever is secured only at its proximal end, said user control mechanism extending from within said handle body via said slot.

2. A surgical knife safety handle as claimed in claim 1, wherein said handle body comprises:
   a distal end, a proximal end and a housing extending along said longitudinal axis between said distal and proximal ends, said housing defining a chamber therein and having said at least one slot extending along said longitudinal axis accessing said chamber, said chamber being at least partially open at said distal end of said handle body; and
   said positioning mechanism slidably mounted in said chamber and having said user control mechanism extending from within said chamber via said slot.

3. A surgical knife safety handle as claimed in claim 2, wherein said handle body comprises said positioning mechanism coupled with a user operable lock for engaging said detent.

4. A surgical knife safety handle as claimed in claim 3, wherein said user operable lock comprises:
   said cantilever integrally formed with said positioning mechanism and resiliently biased toward said slot; and
   a projection disposed on said cantilever for engagement with said detent to substantially secure said positioning mechanism in a fully extended position.

5. A surgical knife safety handle as claimed in claim 3, wherein said detent comprises at least one of a recess, a cavity, a notch or an opening in said handle body.

6. A surgical knife safety handle as claimed in claim 1, wherein said guard comprises said enlargement on a first side of said guard, and comprises a substantially flat second side opposite said first side.

7. A surgical knife safety handle as claimed in claim 6, wherein said substantially flat second side opposite said first side is open between said distal end of said guard and said handle body.

8. A surgical knife safety handle as claimed in claim 6, wherein said distal end of said guard is inclined between said first side and said second side, whereby said second side is shorter than said first side.

9. A surgical knife safety handle as claimed in claim 1, wherein said guard is constructed of transparent material.

10. A surgical knife safety handle as claimed in claim 1, wherein said guard is constructed of an opaque material.

11. A surgical knife safety handle as claimed in claim 1, wherein said distal end of said handle body comprises a textured nonslip surface.

12. A surgical knife safety handle as claimed in claim 1, wherein said enlarged distal end of said guard extends beyond an outer perimeter of said handle body.

13. A surgical knife safety handle, comprising:
   a handle body having a distal end, a proximal end and a slot extending along a portion of said longitudinal axis and at least one detent adjacent to said slot;
   a knife holder for carrying a knife blade at a distal end of said handle body; and
   a guard for selectively covering or exposing said knife blade, said guard having an enlarged distal end to facilitate user contact with said enlarged distal end for handle orientation and control; and
   a user control mechanism disposed upon a cantilever, wherein said cantilever is secured only at its proximal end, said user control mechanism extending from within said handle body via said slot,
   wherein said detent releasably secures at least one of said knife holder and said guard at a position with respect to said handle body.

14. A surgical knife safety handle as claimed in claim 13, wherein said guard is constructed of a transparent material.

15. A surgical knife safety handle as claimed in claim 13, wherein said guard is constructed of an opaque material.

16. A surgical knife safety handle as claimed in claim 13, wherein at least one of said distal end of said handle body and said guard comprises a textured nonslip surface.

17. A surgical knife safety handle as claimed in claim 13, wherein at least one of said knife holder and said guard is configured to be longitudinally moveable with respect to said handle body.

18. A surgical knife safety handle as claimed in claim 17, further comprising:
   said positioning mechanism allowing a user to longitudinally move said at least one of said knife holder and said guard to selectively expose or cover said knife blade.

19. A surgical knife safety handle as claimed in claim 13, wherein said enlarged distal end of said guard extends beyond an outer perimeter of said handle body.

20. A surgical knife safety handle, comprising:
   a handle body having a distal end, a proximal end, a slot extending along a portion of said longitudinal axis and at least one detent adjacent to said slot;
   a knife holder for carrying a knife blade at a distal end of said handle body; and
   a guard for selectively covering or exposing said knife blade, said guard having a cylindrical distal end to facilitate user contact with said distal end for handle orientation and control; and
   a user control mechanism disposed upon a cantilever, wherein said cantilever is secured only at its proximal end, said user control mechanism extending from within said handle body via said slot,
   wherein said detent releasably secures said at least one of said knife holder and said guard at a position with respect to said handle body.

21. A surgical knife safety handle as claimed in claim 20, wherein said guard is constructed of a transparent material.

22. A surgical knife safety handle as claimed in claim 20, wherein said guard is constructed of an opaque material.

23. A surgical knife safety handle as claimed in claim 20, wherein at least one of said distal end of said handle body and said guard comprises a textured nonslip surface.

24. A surgical knife safety handle as claimed in claim 20, wherein at least one of said knife holder and said guard is configured to be longitudinally moveable with respect to said handle body.

25. A surgical knife safety handle as claimed in claim 24, further comprising:
   said positioning mechanism for allowing a user to longitudinally move said at least one of said knife holder and said guard to selectively expose or cover said knife blade.

26. A surgical knife safety handle as claimed in claim 20, wherein said cylindrical distal end of said guard extends beyond a distal edge of said handle body.

27. A surgical knife safety handle with a handle body, a knife holder, and a guard, comprising:
   a positioning mechanism for allowing a user to longitudinally move at least one of a knife holder and a guard to selectively expose or cover a knife blade, said positioning mechanism slidably mounted in a handle body chamber and having a user control mechanism disposed upon a cantilever, wherein said cantilever is secured only at its proximal end, said user control mechanism extends from within said handle body via a slot, and extends along a portion of a longitudinal axis of said handle body; and
   a detent adjacent to said slot, wherein said positioning mechanism is configured to engage said detent.

28. A surgical knife safety handle as claimed in claim 27, wherein said user control mechanism comprises:
   said cantilever resiliently biased toward said slot; and
   a projection disposed on said cantilever for engagement with said detent to substantially secure said positioning mechanism in one of a fully extended position and a fully retracted position.

29. A surgical knife safety handle as claimed in claim 27, wherein said detent comprises at least one of a recess, a cavity, a notch or an opening in said handle body.

30. A surgical knife safety handle as claimed in claim 27, wherein said guard comprises an enlarged distal end which extends beyond an outer perimeter of said handle body.

\* \* \* \* \*